US012053521B2

(12) United States Patent
Yushin et al.

(10) Patent No.: US 12,053,521 B2
(45) Date of Patent: Aug. 6, 2024

(54) NANOFIBER COMPOSITIONS FOR A VACCINE ADJUVANT, POROUS SCAFFOLD OR POROUS MEMBRANE

(71) Applicant: Sila Nanotechnologies Inc., Alameda, CA (US)

(72) Inventors: Gleb Yushin, Atlanta, GA (US); Kostiantyn Turcheniuk, Atlanta, GA (US); Kyle Kulinski, Oakland, CA (US)

(73) Assignee: SILA NANOTECHNOLOGIES, INC., Alameda, CA (US)

( * ) Notice: Subject to any disclaimer, the term of this patent is extended or adjusted under 35 U.S.C. 154(b) by 553 days.

(21) Appl. No.: 16/877,185

(22) Filed: May 18, 2020

(65) Prior Publication Data

US 2020/0360513 A1 Nov. 19, 2020

Related U.S. Application Data

(60) Provisional application No. 62/849,619, filed on May 17, 2019.

(51) Int. Cl.
*A61K 39/39* (2006.01)
*A61K 39/00* (2006.01)

(52) U.S. Cl.
CPC .... *A61K 39/39* (2013.01); *A61K 2039/55505* (2013.01); *A61K 2039/55511* (2013.01); *A61L 2400/12* (2013.01)

(58) Field of Classification Search
CPC .... C04B 2235/5445; C04B 2235/3217; C04B 2235/441; C04B 2235/5454; C04B 2235/322; C04B 2235/656; C04B 2235/96; C04B 35/4885; C04B 35/6262; C04B 35/6263; C04B 35/6264; C04B 35/62655;

(Continued)

(56) References Cited

U.S. PATENT DOCUMENTS

| | | | |
|---|---|---|---|
| 2011/0151255 A1* | 6/2011 | Kim | C04B 35/6225 428/401 |
| 2014/0332733 A1* | 11/2014 | Joo | D04H 1/4234 423/608 |

FOREIGN PATENT DOCUMENTS

| | | | | |
|---|---|---|---|---|
| CN | 111217382 A | * | 6/2020 | C01F 7/02 |
| JP | 2013212997 A | * | 10/2013 | |

(Continued)

OTHER PUBLICATIONS

Wang, Xiupeng; Li, Xia; Sogo, Yu; Ito, Atsuo; "Simple synthesis route of mesoporous AlOOH nanofibers to enhance immune response"; RSC Advances, 2013, 3, 8164; (Year: 2013).*

(Continued)

*Primary Examiner* — Jennifer A Steele
(74) *Attorney, Agent, or Firm* — Muncy, Geissler, Olds & Lowe, P.C.; Daniel Podhajny

(57) ABSTRACT

An aspect is directed to a vaccine adjuvant including a nanofiber that comprises an oxide or a salt of one, two, three or more metals selected from the group of Al, Ca, Mg, Li, Na, K, La, Y, Si, Fe and Zn. Another aspect is directed to a porous scaffold or a porous membrane that comprises nanofibers comprising an oxide or a salt of one, two, three or more metals selected from the group of Al, Ca, Mg, Li, Na, K, La, Y, Si, Fe and Zn, where the porous scaffold or the porous membrane is configured for use in an environment where the nanofibers are exposed to a direct contact with extracellular body fluids.

22 Claims, 7 Drawing Sheets

(58) Field of Classification Search
CPC ........ C04B 35/62675; C04B 35/62813; C04B 35/62823; C04B 35/62886; C04B 35/62892; C04B 2235/40; C04B 2235/5436; C04B 2235/9607; C04B 35/106; C04B 41/4531; C04B 41/4535; C04B 2235/3206; C04B 2235/3208; C04B 2235/3215; C04B 2235/3232; C04B 2235/3244; C04B 2235/3272; C04B 2235/3275; C04B 2235/3418; C04B 2235/405; C04B 2235/443; C04B 2235/483; C04B 2235/6565; C04B 2235/6567; C04B 2235/80; C04B 35/14; C04B 35/26; C04B 35/62236; C04B 35/624; C04B 35/74; C04B 35/10; C04B 38/06; D01D 5/0007; D01D 5/0038; D01D 5/004; D01D 5/0061; D01D 5/0084; A61K 39/39; A61K 2039/55505; A61K 2039/55511; A61K 2039/55555; Y02A 50/30; A61L 2400/12; B82Y 30/00; B82Y 40/00; B82Y 10/00; B82Y 20/00; C01P 2006/17; C01P 2006/16; C01P 2006/14; C01P 2004/64
See application file for complete search history.

(56) References Cited

FOREIGN PATENT DOCUMENTS

| KR | 20140136993 A | * | 12/2014 | |
|---|---|---|---|---|
| RU | 2304463 C2 | * | 8/2007 | ........... A61L 2/0017 |
| RU | 2008143241 A | * | 5/2010 | ............... A61L 9/16 |
| RU | 2560432 C2 | * | 8/2015 | ............. A61K 33/08 |
| WO | WO-03000407 A1 | * | 1/2003 | ........... A61L 2/0017 |
| WO | WO-2013033367 A1 | * | 3/2013 | ............ A61K 31/202 |
| WO | WO-2014189412 A1 | * | 11/2014 | ............. A61K 33/08 |

OTHER PUBLICATIONS

Li, Xia; Wang, Xiupeng; Ito, Atsuo; "Tailoring inorganic nanoadjuvants towards next generation vaccines"; Chem. Soc. Rev., 2018, 47, 4954 (Year: 2018).*

Bilyy et al., "Aluminum oxide nanowires as safe and effective adjuvants for next-generation vaccines," Materials Today, vol. 22, Jan./Feb. 2019, pp. 58-66.

* cited by examiner

NANOFIBER COMPOSITIONS FOR A VACCINE ADJUVANT, POROUS SCAFFOLD OR POROUS MEMBRANE

CROSS-REFERENCE TO RELATED APPLICATIONS

The present application for patent claims the benefit of U.S. Provisional Application No. 62/849,619, entitled "NANOFIBER COMPOSITION, MORPHOLOGY AND SYNTHESIS FOR USE IN CONTACT WITH EXTRA-CELLULAR BODY FLUIDS," filed May 17, 2019, which is expressly incorporated herein by reference in its entirety.

BACKGROUND

Field

Embodiments of the present disclosure relate generally to the design, composition, morphology, microstructure, fabrication and applications of nanofibers and their use in medical and biomedical fields in contact with body fluids. Examples of such uses may include but are not limited to more efficient and safer immunologic adjuvants for vaccines, improved adjuvants for other medical needs (e.g., anesthesia adjuvants, adjuvant analgesic, etc.), means for faster regeneration of nerves, means for faster curing of wounds and cuts, more efficient and more convenient ways to incorporate antiseptic agents that reduce or prevent bacteria or virus growth, among others.

Background

Owing in part to their relatively high surface area, small dimensions, flexibility, some nanofibers may exhibit interactions with various bodily liquids markedly different from those of micron-scale powders or micron-scale fibers of the same composition and, in some cases, much more favorable in certain applications. However, despite seemingly promising properties demonstrated by some of the nanofibers, further development is needed, particularly for potential applications where nanofibers exhibit a direct contact with body fluids, such as extracellular fluids. Further improvements in safety, reduced or eliminated unfavorable side effects and enhancement of favorable properties are needed.

Accordingly, there remains a need for improved nanofibers for more favorable interactions with body fluids and reduced or eliminated undesirable side reactions in a broad range of medical and biomedical applications. There additionally remains a need for improved materials in such nanofibers and improved manufacturing processes of such nanofibers.

SUMMARY

Embodiments disclosed herein address the above stated needs by providing improved performance of nanofibers for medical applications, where they exhibit a direct contact with body liquids, such as various extracellular body fluids and various intracellular fluids.

One particular embodiment is directed to a vaccine adjuvant, comprising a nanofiber with a diameter in the range from around 1 nm to around 500 nm, a length in the range from around 250 nm to around 500 μm, an aspect ratio in the range from around 10 to around 100,000, a total internal open pore volume in the range from around 0.01 cm3/g to around 3 cm3/g, and an average pore size in the range from around 0.5 nm to around 50 nm, wherein the nanofiber comprises an oxide or a salt of one, two, three or more metals selected from the group of Al, Ca, Mg, Li, Na, K, La, Y, Si, Fe and Zn.

Another particular embodiment is directed to a porous scaffold or a porous membrane, comprising nanofibers with an average diameter in the range from around 1 nm to around 500 nm, an average length in the range from around 250 nm to around 500 μm, an average aspect ratio in the range from around 10 to around 100,000, an average total internal open pore volume in the range from around 0.01 cm3/g to around 3 cm3/g, and an average pore size in the range from around 0.5 nm to around 50 nm, wherein the nanofibers comprise an oxide or a salt of one, two, three or more metals selected from the group of Al, Ca, Mg, Li, Na, K, La, Y, Si, Fe and Zn, and wherein the porous scaffold or the porous membrane is configured for use in an environment where the nanofibers are exposed to a direct contact with extracellular body fluids.

BRIEF DESCRIPTION OF THE DRAWINGS

The accompanying drawings are presented to aid in the description of embodiments of the disclosure and are provided solely for illustration of the embodiments and not limitation thereof. Unless otherwise stated or implied by context, different hatchings, shadings, and/or fill patterns in the drawings are meant only to draw contrast between different components, elements, features, etc., and are not meant to convey the use of particular materials, colors, or other properties that may be defined outside of the present disclosure for the specific pattern employed.

DETAILED DESCRIPTION

Figure 1:
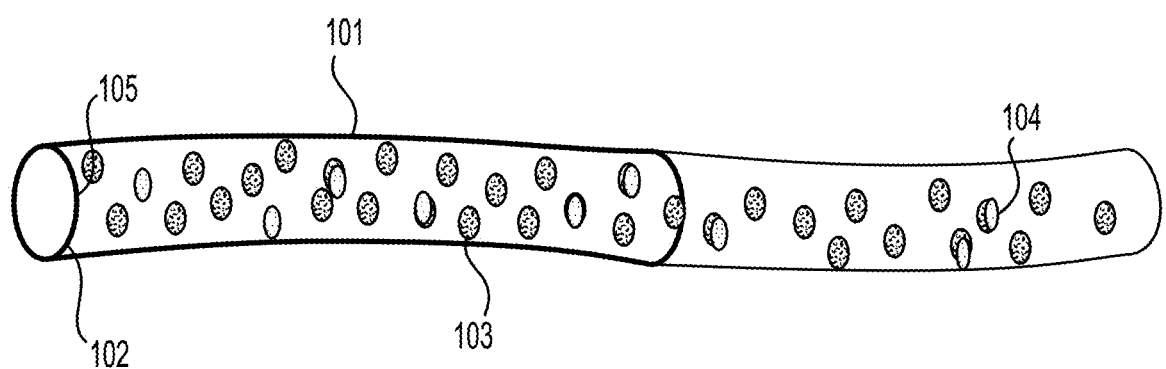
FIG. 1 illustrates an example nanofiber in which the microstructure, morphology, dimensions, composition and fabrication method(s) described herein, or combinations thereof, may be applied according to various embodiments.

Aspects of the present invention are disclosed in the following description and related drawings directed to specific embodiments of the invention. The term "embodiments of the invention" does not require that all embodiments of the invention include the discussed feature, advantage, process, or mode of operation, and alternate embodiments may be devised without departing from the scope of the invention. Additionally, well-known elements of the invention may not be described in detail or may be omitted so as not to obscure other, more relevant details. Further, the terminology of "at least partially" is intended for interpretation as "partially, substantially or completely".

Any numerical range described herein with respect to any embodiment of the present invention is intended not only to define the upper and lower bounds of the associated numerical range, but also as an implicit disclosure of each discrete value within that range in units or increments that are consistent with the level of precision by which the upper and lower bounds are characterized. For example, a numerical distance range from 7 nm to 20 nm (i.e., a level of precision in units or increments of ones) encompasses (in nm) a set of [7, 8, 9, 10, . . . , 19, 20], as if the intervening numbers 8 through 19 in units or increments of ones were expressly disclosed. In another example, a numerical percentage range from 30.92% to 47.44% (i.e., a level of precision in units or increments of hundredths) encompasses (in %) a set of [30.92, 30.93, 30.94, . . . , 47.43, 47.44], as if the intervening numbers between 30.92 and 47.44 in units or increments of hundredths were expressly disclosed. Hence, any of the intervening numbers encompassed by any disclosed numerical range are intended to be interpreted as if those intervening numbers had been disclosed expressly, and any such intervening number may thereby constitute its own upper and/or lower bound of a sub-range that falls inside of the broader range. Each sub-range (e.g., each range that includes at least one intervening number from the broader range as an upper and/or lower bound) is thereby intended to be interpreted as being implicitly disclosed by virtue of the express disclosure of the broader range.

Some examples below characterize numerical values using approximations (e.g., terms such as "about", "around", "approximately", "~", etc.). In some designs, such approximations may be accurate to either to a degree commensurate with the relevant instrumentation (e.g., scanning electron microscope (SEM), gas chromatograph, etc.) for measuring the associated value, or to a degree in which that value would be rounded to at an associated level of precision (e.g., whichever is greater). For example, "about 4" may encompass any value between 3.5 and 4.5, "about 4.0" may encompass any value between 3.95 and 4.05", "about 4.00" may encompass any value between 3.995 and 4.005, and so on.

While the description of one or more embodiments below may describe certain examples in the context of aluminum- (Al-) or oxygen- (O-) comprising small (nano)wires, (nano)whiskers, (nano)fibers, (nano)ribbons, other elongated (nano)particles, including various porous elongated particles, it will be appreciated that various aspects may be applicable to other compositions (such as other metal oxides as well as metal hydroxides, metal oxyhydroxides, metal alkoxides, metal hydroxy alkoxides, metal alkoxy oxides, metal oxynitrides, metal phosphate, metal phosphate hydroxides, metal sulfate, and various other ceramic elongated particles that comprise metal compositions). Examples of suitable metal (or semimetal) atoms for such compositions may include (but are not limited to) at least one of the following (depending on the particular application) or their combination: Al, Mg, Ca, Li, Na, K, Cs, Sr, Ti, Fe, Cu, Ag, Zn, to name a few.

While the description of one or more embodiments below may describe certain examples in the context of small nanowires, nanowhiskers, nanotubes, nanofibers, nanoribbons, other elongated nanoparticles, including various porous elongated nanoparticles that comprise a single metal (for example, aluminum) in their composition, it will be appreciated that various aspects may be applicable to compositions that comprise two, three or more metals.

While the description of one or more embodiments below may describe certain examples in the context of pure metal oxides, it will be appreciated that various aspects may be applicable to compositions that may comprise both oxide and some fraction of oxide adjacent species such as hydroxides (where hydrogen atoms are bonded to oxygen atoms), suboxides (where oxygen atoms are bonded to oxygen atoms), carboxylates (where metal atoms are bonded to carbonate groups), alkoxides (where metal atoms are bonded to alkoxide groups), hydrides (where metal atoms are bonded to hydrogen), nitrides (where metal atoms are bonded to nitrogen), hydroxides (where metal atoms are bonded to hydroxylic group —OH), phosphates, and sulfates, among many others. As such, the coordination number for metal atoms in such compositions may vary from that of the pure oxides.

While the description of one or more embodiments below may describe certain examples in the context of pure alkoxides, it will be appreciated that various aspects may be applicable to compositions that may contain both alkoxide and some fraction of alkoxide adjacent species, such as hydroxides (containing hydrogen bonded to an oxo group), suboxides (containing oxygen bonded to oxo group), carboxylate (oxo group bonded to carbonate groups), nitride (oxo group bonded to nitrogen), among many others. The structure of pure alkoxide may contain bridging alkoxide groups (where oxygen of alkoxide is bonded to two or more metal atoms) and terminal alkoxide groups (where oxygen of alkoxide is bonded to one metal atom). Note that in the compositions that may contain both alkoxide and one or more other species (such as hydroxide alkoxides, suboxide alkoxide, carboxylate alkoxides, nitride alkoxides, among many others), either the alkoxide or the other group(s) may occupy bridging or terminal positions. As such, the coordination number for metal atoms in such compositions may vary from that of the pure alkoxides and the ratio of the alkoxide groups (—RO) to metal atoms may vary from that of the pure alkoxides. For example, in case of aluminum ethoxide compositions, the aluminum (Al) atoms may not be 6-coordinated (as expected for pure $Al(EtO)_3$), but may, for example, comprise 6-coordinated, 5-coordinated, 4-coordinated and 3-coordinated Al atoms. Similarly, the molar ratio of ethoxide groups (-EtO) to Al atom may not be 3 (as expected for pure $Al(EtO)_3$), but may, for example, range from as high as around 10 to as low as around 0.1. Similarly, Al ethoxide can comprise of ethoxide, hydroxide and ethanol ligands, such as $Al(EtO)_{3-(x+y)}(OH)_x(EtOH)_y$, where x and y range from as high as 3 to as low as 0.001. Similarly, ethoxide, hydroxide and ethanol ligands may occupy bridging or terminal positions.

While the description of one or more embodiments below may describe certain examples in the context of monomeric alkoxides, it will be appreciated that various aspects may be applicable to compositions that may contain oligomeric and polymeric alkoxides than may contain from about 1 to about 1,000,000,000 repeat units. Examples of such alkoxides may include aluminum ethoxide compositions such as $[Al(EtO)_{3-(x+y)}(OH)_x(EtOH)_y]_n$, where x and y may range from as high as 3 to as low as 0.001 and n may range from about 1 to about 1,000,000,000. Similarly, monomer units in oligomers and polymers may comprise chemically different units, where ligand positions may be different. Similarly, monomer units in oligomers and polymers may comprise 6-coordinated, 5-coordinated, 4-coordinated and 3-coordinated Al atoms. Similarly, oligomeric and polymeric alkoxides may exhibit different tacticity, molecular weight and polydispersity index.

In the context of one or more embodiments of the present description, the term "bulk" (as in "bulk nanofibers", "bulk particles", "bulk fibers", etc.) refers to a sample where particles (such as nanofibers and other small particles, etc.) are stuck together by chemical, electrostatic, and/or physical mechanisms so as to form large agglomerates (e.g., agglomerates having average dimensions in the range from about 1 µm to about 10 cm).

In the context of one or more embodiments of the present description, the term "aspect ratio" refers to the ratio of the longest dimension to the shortest dimension of a material or a particle.

In the context of one or more embodiments of the present description, the term "dispersion" refers to a mixture of solid(s) and liquid(s) whereas the solid(s) interact(s) with the liquid(s) in a way which changes the fluid properties of both the solid(s) and liquid(s). For example, solid (nano)particles of various shapes and sizes may be dispersed in a liquid causing the viscosity of the liquid to increase and the Brownian motion of the particles to increase. The term "dispersion" may further refer to the condition where solid (nano)particles of various shapes and sizes are being suspended in a liquid (solvent). In the context of one or more embodiments of the present description, the term "stable dispersion" refers to the conditions where particles (such as fibers, flakes, nanoparticles or particles of various other shapes and sizes) remain suspended for a timescale that is sufficient for a given processing stage (e.g., such as casting the dispersion into a film on a substrate, injecting a vaccine of sufficiently uniform composition, etc.).

While the description of one or more embodiments below may also describe certain examples in the context of the formation and applications of certain oxides of metal(s) (of dense or porous particles of various shapes, including but not limited to fiber-shapes), it will be appreciated that various aspects of the present disclosure may be applicable to the formation of other ceramic materials (not necessarily oxides) as well as various ceramic-ceramic, ceramic-glass, ceramic-metal, ceramic-carbon, ceramic-polymer, glass-polymer, glass-ceramic-polymer, polymer-polymer and other composites.

As used herein, elongated particles (such as dense and porous nanofibers, nanowires, whiskers, nanotubes, nanoribbons, etc.) of suitable size (e.g., diameter [or, more generally, average cross-sectional dimensions in the direction perpendicular to the elongation direction] from around 1.0 nm to around 950.0 nm), shape, aspect ratios, density, porosity, crystal structure, and morphology may be generally referred to herein as "nanofibers." In one or more embodiments of the present disclosure, the suitable diameter (or width) of individual small fibers (of various compositions) may range from around 1 nm to around 500 nm, in some designs, from around 5.0 nm to around 500.0 nm and the suitable length of individual small fibers (of various compositions) may range from around 50.0 nm to around 5 mm (in some designs, an average length may range from around 250 nm to around 500 μm; in other designs an average length may range from around 50 nm to around 2.5 micron; in other designs an average length may range from around 2.5 micron to around 25 micron; in yet other designs an average length may range from around 25 micron to around 100 micron; in yet other designs an average length may range from around 100 micron to around 5 mm). In one or more embodiments of the present disclosure, the suitable aspect ratio (width-to-length) of individual small fibers (of various compositions) may preferably range from around 1:10 to around 1:1,000,000 (in some designs, from around 1:10 to around 1:100,000; in some designs, from around 1:10 to around 1:100; in other designs from around 1:100 to around 1:1,000; in other designs from around 1:100 to around 10,000; in other designs from around 1:1,000 to around 10,000; in other designs from around 1:10,000 to around 1:100,000, in other designs from around 100,000 to around 1,000,000). Too high aspect ratio may make it difficult for the nanofibers to be properly dispersed in an adjuvant formulation, while too low aspect ratio may make them less effective. In some designs, an aspect ratio in the range from around 1:10 to around 1:100,000 (in some designs, from around 1:100 to around 1:10,000) may be advantageously used.

In some designs, a plurality of nanofibers with diameters in the range from around 1 nm to around 500 nm, lengths in the range from around 250 nm to around 500 μm, and aspect ratios in the range from around 10 to around 100,000 may be used as part of a vaccine adjuvant. In an example, a total weight fraction of the plurality of nanofibers relative to all other inorganic metal oxides or inorganic metal salts in the adjuvant composition may range from around 10 wt. % to around 100 wt. %.

In some designs and applications, the individual nanofibers may be agglomerated into bundles or into flexible threads or into flexible yarns and may be parts of woven and nonwoven fabrics or filters/membranes. In some designs and applications, the individual nanofibers may be spun into larger (e.g., composite) nanofibers that additionally comprise other materials (e.g., salts, metals, polymers, etc.). These, in turn, may also be parts of woven and nonwoven fabrics or filters/membranes in some designs.

Depending on the application, in an example, the suitable true density (taking into consideration closed porosity) of nanofibers may range from around 0.3 to around 4 $g/cm^3$ (e.g., for particles comprising only Al metal in their composition) and to around 6 $g/cm^3$ (e.g., for particles comprising metals other than Al in their composition) in the context of one or more embodiments of the present description. Depending on the application and the processing conditions, in an example, the suitable pore volume (e.g., open pore volume) within individual nanofibers may range from around 0 to around 5 $cm^3/g$ (e.g., in some designs, from around 0.01 $cm^3/g$ to around 3 $cm^3/g$; in some designs, from around 0.05 $cm^3/g$ to around 1 $cm^3/g$). Depending on the application and the processing conditions, in an example, the microstructure may range from amorphous to nanocrystalline to polycrystalline to single crystalline to a mixture of those to other types. Depending on the application and processing conditions, in an example, the suitable surface roughness of the nanofibers may range from around 0 nm to around 100 nm.

FIG. 1 illustrates an example nanofiber 101 in which the microstructure, morphology, dimensions, composition and fabrication method(s) described herein, or combinations thereof, may be applied according to various embodiments. In this illustrative example, the nanofiber 101 of suitable composition has a near-spherical cross-section 102, comprises pores 103 of suitable dimensions, some of which are filled with a suitable functional filler material 104. An external coating 105 encases a part of the nanofiber 101.

A vaccine adjuvant is a material that enhances the body's immune response to an antigen. Adjuvants have been successfully used in human and animal vaccinations for more than half a century. The benefits of adjuvant incorporation into vaccines balances the risks of the appearances of adverse side effects such as pain, local inflammation, swelling, injection site necrosis, lymphadenopathy, granulomas, ulcers and the generation of sterile abscesses, nausea, fever, adjuvant arthritis, uveitis, eosinophilia, allergy, anaphylaxis, organ specific toxicity and immunotoxicity, i.e. cytokines release, immunosuppression or autoimmune diseases. The benefits obtained from vaccine adjuvants often correlate with their toxicity, thus limiting the toxicity of adjuvants remains a challenge.

Commercial adjuvant particles commonly comprise Al-based salts, most commonly aluminum oxyhydroxide (AlOOH), aluminum hydroxide (Al(OH)$_3$), aluminum potassium sulfate (KAl(SO$_4$)$_2$) and others. Despite their broad use, their adjuvant properties are rather moderate and, additionally, often induce undesired side effects, such as damages to microvasculature. Conventional adjuvant salt particles exhibit random shape, relatively large size (often above 500 nm in average dimensions), relatively small surface area (often below around 50 or even 5 m$^2$/g, when measured using N$_2$ sorption and analyzed using so-called BET method/equation) and poorly controlled microstructure, morphology and surface chemistry. Many less cytotoxic and more robust (in terms of stability or performance sensitivity to vaccination conditions or other factors) compositions of the adjuvants (e.g., oxides, etc.) are not typically used because of their poor efficacy as adjuvants.

In some designs, nanofiber-shaped adjuvants of various compositions may enable safer, more efficient, more robust and/or cheaper vaccines. Nanofiber-shaping of adjuvants may enhance immune response of vaccines (relative to regularly shaped adjuvants) and thus enable high vaccine efficiency either with reduced adjuvant amount/weight (and thus reduced potential side-effects) or reduced active component amount (and thus reduced cost) or both. In some designs, certain compositions and properties of such nanofiber adjuvants (e.g., morphology, microstructure, dimensions, aspect ratio, porosity, external surface area, density, surface charge, etc.) contribute to their superior performance. Embodiments described below in more detail relate to specific examples of such properties and describes a few exemplary routes for producing such nanofibers.

In some designs, ~20-60 micron long, ~20-40 nm diameter polycrystalline γ-$Al_2O_3$ nanowires with ~20 nm grain size may be used in vaccine adjuvants so as to exhibit strong humoral and/or cellular immune responses with little inflammation after 35 days. In one or more embodiments of the present disclosure, other types of nanofibers (e.g., with different composition or microstructure or dimensions or morphology or/and other properties and their combinations) may be advantageously used as adjuvants with remarkable and highly desirable performance characteristics (e.g., strong immune response, favorable performance in a broad range of vaccines, reduced inflammation after 5-35 days, reduced damages to microvascular, fewer (if any) other side effects, among others). In addition, one or more embodiments of the present disclosure are directed to advantageous use of these and other nanofibers (e.g., composite nanofibers, etc.) of similar dimensions and variable compositions (MgO, CaO, Mg—Ca—O, $Al_2O_3$, Al—Mg—O, many others) for a range of other medical and biomedical applications.

In some designs, it may be advantageous for the diameter of the nanofibers to range from around 1 nm to around 500 nm. In some designs, the optimal range may depend on the specific vaccines, vaccine media, other additive composition and amount and, of course, properties of nanofibers (such as composition, morphology, crystal structure, porosity, etc.). So, in some designs, the most preferable diameter (more generally—average cross-sectional dimension in the direction perpendicular to the fiber axis/length) may range, for example, from around 1 nm to around 5 nm; from around 5 nm to around 20 nm; from around 20 nm to around 40 nm; from around 40 nm to around 60 nm; from around 60 nm to around 80 nm; from around 80 nm to around 100 nm; from around 100 nm to around 150 nm; from around 150 nm to around 250 nm; or from around 250 nm to around 500 nm.

Furthermore, in some designs, it may be advantageous for the nanofiber diameter to change (in some designs—be reduced; in some design—be increased; in some designs—to initially increase and then decrease, etc.) after a direct contact with extracellular body fluids or biological fluids (e.g., blood plasma, lymph, interstitial fluid, transcellular fluid, etc.) and/or body cells. For example, the nanofiber diameter may initially swell upon coming into contact with the body fluids, and may thereafter gradually dissolve into the body fluids. In some designs, for example, it may be advantageous for the nanofiber diameter to be reduced by around 10% to around 100% (almost completely disappear/dissolve) from around 2 days to around 60 days after the exposure.

In some designs, it may generally be advantageous for the length of the nanofibers to range from around 50 nm to around 1 mm. In some designs, the optimal range may depend on the specific vaccines, vaccine media, other additive composition and amount and, of course, properties of nanofibers (such as composition, morphology, crystal structure, porosity, etc.). In some designs, the optimal length may range, for example, from around 50 nm to around 500 nm; from around 500 nm to around 2000 nm (or 2 micron); from around 2 micron (μm) to around 20 μm; from around 20 μm to around 60 μm; from around 60 μm to around 100 μm; from around 100 μm to around 200 μm; or from around 200 μm to around 1 mm. In some designs, the optimal nanofiber length may range around 250 nm to around 500 μm (in some designs, in a more narrow range, such as from around 1.5 μm to around 150 μm).

In some designs, it may be advantageous to combine nanofibers of different diameters or lengths or aspect ratios in a single formulation or application (e.g., have different subsets of the nanofibers with average diameters that vary by about 10-100 times or having length of nanofibers vary by about 5-5000 times) in order to achieve a combination of more favorable properties/performance as adjuvants. In some designs, different dimensions of nanofibers may advantageously exhibit different compositions or porosities.

In some designs, it may generally be advantageous for Brunauer-Emmett-Teller (BET) specific surface area (SSA) of the nanofibers to range from around 20.0 $m^2/g$ to around 4000.0 $m^2/g$. In some designs, the optimal range may depend on the specific vaccines, vaccine media, other additive composition and amount and, of course, properties of nanofibers (such as composition, morphology, crystal structure, porosity, etc.). In some designs, the optimal BET SSA may range, for example, from around 20.0 $m^2/g$ to around 50.0 $m^2/g$; from around 50.0 $m^2/g$ to around 100.0 $m^2/g$; from around 100.0 $m^2/g$ to around 250.0 $m^2/g$; from around 250.0 $m^2/g$ to around 500.0 $m^2/g$; from around 500.0 $m^2/g$ to around 1000.0 $m^2/g$, or from around 1000.0 $m^2/g$ to around 4000.0 $m^2/g$. In some designs, a higher specific surface area may generate a stronger immune response. In some designs, a higher specific surface area may generate a more extensive formation of neutrophil extracellular traps (NETs), which may help to effectively isolate nanofibers and suppress local self-limiting inflammation.

Furthermore, in some designs, it may be advantageous for the BET SSA of the nanofibers to change (in some designs—be reduced; in some designs—be increased; in some designs—to be initially reduced and then increased; in some designs—to initially increase and then decrease) after a direct contact with extracellular body fluids or biological fluids (e.g., blood plasma, lymph, interstitial fluid, transcellular fluid, etc.) and/or body cells. For example, the nanofiber BET SSA may initially increase upon coming into contact with the body fluids and may thereafter gradually be reduced into the body fluids. In some designs, for example, it may be advantageous for the nanofiber diameter to change by around 10% to around 100% (e.g., almost completely disappear/dissolve) from around 2 days to around 60 days after the exposure.

In some designs, it may generally be advantageous for nanofibers to comprise pores. In some designs, pores in the nanofibers may be utilized to effectively adsorb and precipitate protein antigens in solution in order to improve vaccine immunogenicity by facilitating slow release of antigen from the vaccine. In some designs, the pore size may be tuned so as to increase antigen adsorption (e.g., range from around the size of the antigens to about five times the size of the antigens). In some designs, some of such pores in the nanofibers may (e.g., at least initially) be closed (e.g., inaccessible to body fluids). In some designs, some of such closed (e.g., at least initially closed) pores may be filled with another functional (useful) material or compound (e.g., an antigen or a metal or metal salt to enhance immune response further or another component of the vaccine in some vaccination-related applications). In some designs, such a filler material may become exposed to body fluids over time to perform desired function(s) (e.g., similar to the timed release of medication into the body from a swallowed pill). In some designs, gradual dissolution of the filler material may open up larger surface of the nanofibers to be exposed to body fluids. As such the filler material may regulate the exposure over time, which may be advantageous in some designs (e.g., control immune response or reduce damages to micro-capillaries, etc.). In some designs, some (or all) of such pores may (e.g., at least initially) be open (accessible to body fluids or vaccine fluids, or air, etc.). In some designs, some of such open pores may be at least partially filled with another functional (useful) material or compound (e.g., an antigen or a metal or metal salt to enhance immune response further or a water-soluble polymer or another component of the vaccine in some vaccination-related applications). Some of the functional filler material may be in the form of nanoparticles. In some designs, the shape of such nanoparticles may be near-spheroidal. In some designs, a larger fraction of such a filler material may become exposed to body fluids over time to perform desired function(s). In some designs, gradual dissolution of the filler material may open up larger surface of the nanofibers to be exposed to body fluids. In some designs, it may generally be advantageous for total (closed and open, combined) pore volume of the nanofibers to range from around 0.01 cc/g to around 3.00 $cm^3/g$. In some designs, it may generally be advantageous for open pore volume of the nanofibers to range from around 0.01 cc/g to around 3.00 $cm^3/g$. In some designs, the optimal range may depend on the specific vaccines, vaccine media, other additive composition and amount and, of course, properties of nanofibers (such as composition, morphology, crystal structure, porosity, etc.). In some cases, larger open pore volume may generate stronger immune response or more extensive formation of NETs. In some designs, it may generally be advantageous for most (e.g., about 50-75% vol. relative to the total pore volume) of the nanofiber pore sizes to range from around 0.30 nm to around 60.0 nm. In some designs, it may generally be advantageous for the average pore size of the nanofibers to range from around 0.5 nm to around 50 nm (e.g., in some designs, from around 0.5 to around 1 nm; in some designs, from around 1 to around 2 nm; in some designs, from around 2 to around 3 nm; in some designs, from around 3 to around 5 nm; in some designs, from around 5 to around 10 nm; in some designs, from around 10 to around 60 nm). In some designs, the nanofiber average pore size may advantageously range from around 0.5 nm to around 20 nm.

In some designs, porous nanofiber adjuvants may comprise metal organic frameworks (MOFs). In some designs, metals in such MOFs may comprise Al. In some designs, metals in such MOFs may comprise magnesium (Mg). In some designs, metals in such MOFs may comprise calcium (Ca). In some designs, metals in such MOFs may comprise potassium (K). In some designs, metals in such MOFs may comprise sodium (Na). In some designs, metals in such MOFs may comprise iron (Fe). In some designs, metals in such MOFs may comprise yttrium (Y), lanthanum (La) or lanthanoids.

In some designs, it may generally be advantageous for nanofibers to exhibit relatively small grain size (e.g., from around 1 nm to around 100 nm in average grain dimensions) or to be fully amorphous (e.g., exhibit grain size from around 0 nm to around 1 nm). In some designs, the nanofibers may comprise both amorphous and nanocrystalline (e.g., about 1-100 nm) regions. In some designs, the size of the grains and the microstructure of the nanofibers may have a significant impact on their interactions with body fluids. In some designs, the optimal microstructure and grain size distribution may depend on the specific vaccines, vaccine media, other additives' composition and amount and, of course, properties of nanofibers (such as composition, morphology, crystal structure, porosity, etc.).

In some designs (e.g., for crystalline or polycrystalline nanofibers), it may be advantageous for the crystal lattice of at least the portion of the nanofiber material to be either cubic or tetragonal or monoclinic or orthorhombic or hexagonal. In some designs, it may be advantageous for the nanofibers to comprise materials of different crystal lattice systems.

In some designs, it may be advantageous for the nanofibers (used in adjuvants) to comprise an oxide or a salt of one, two, three or more metals selected from the group of Al, Ca, Mg, Li, Na, K, La, Y, Si, Fe and Zn. In some designs, it may be advantageous for a metal oxide or a metal salt of the nanofiber to be selected from one, two or more of the following: (i) metal oxide, (ii) metal hydroxide, (iii) metal oxyhydroxide, (iv) metal sulfate, (v) metal carbide, (vi) metal phosphate, (vii) metal hydroxy phosphate, (viii) metal hydroxy phosphate sulfate, (ix) metal phosphate sulfate, (x) metal hydroxy sulfate, (xi) metal carbonate, (xii) metal carbonate phosphate, and (xiii) metal silicate. In some designs, it may be advantageous for the nanofibers to comprise two or more metals with the atomic fraction (relative to all metals in the oxide or salt) of more than about 0.01 at. %.

In some designs, it may be advantageous for the nanofibers (or, in case of the composite nanofibers, at least for one or more of the components of the nanofibers) to comprise aluminum (Al) atoms. In some designs, it may be advantageous for the amount of Al to comprise about 20-100% of all the metals in the nanofiber composition. Examples of such Al-containing composition(s) of the nanofibers or nanofiber components may include, but are not limited to: various types (crystal structures) of aluminum oxide ($Al_2O_3$) (e.g., amorphous $Al_2O_3$, cubic $\gamma$-$Al_2O_3$, cubic $\eta$-$Al_2O_3$, monoclinic $\theta$-$Al_2O_3$, hexagonal $\chi$-$Al_2O_3$, orthorhombic $\kappa$-$Al_2O_3$, $\delta$-$Al_2O_3$ (that can be tetragonal or orthorhombic), $\alpha$-$Al_2O_3$, among others or their various combinations) including "doped" $Al_2O_3$ (where Na or K or Li or Mg or Ca or Sr or Ti or Fe or Zn or La or Y or other metals may be present in addition to Al in a relatively small content of less than around 10 at. %; in some designs from around 0.0001 at. % to around 1 at. %); aluminum hydroxide (Al(OH)$_3$) as well as hydroxides of mixed metals that comprise at least about 50 at. % of Al relative to other metals (e.g., Na, K, Li, Mg, Ca, Sr, Ti, Fe, Si, Zn, La, Y, etc.) (e.g., as in LiAl(OH)$_4$ or NaAl(OH)$_4$ or MgAl(OH)$_5$ etc.); aluminum oxyhydroxide AlO(OH) as well as oxyhydroxides of mixed metals (e.g., Na, K, Li, Mg, Ca, Sr, Ti, Fe, Si, Zn, La, Y, etc.) that comprise at least about 50 at. % of Al relative to other metals (and where other metals may comprise from around 0.0001 at. % to around 50 at. %); aluminum carbide (Al$_4$C$_3$) as well as carbides of mixed metals that comprise at least about 50 at. % of Al relative to other metals (e.g., where other metals (e.g., Na, K, Li, Mg, Ca, Sr, Ti, Fe, Si, Zn, La, Y, etc.) may comprise from around 0.0001 at. % to around 50 at. %); aluminum phosphate (AlPO$_4$) as well as phosphates of mixed metals that comprise at least about 50 at. % of Al relative to other metals (e.g., where other metals (e.g., Na, K, Li, Mg, Ca, Sr, Ti, Fe, Si, Zn, La, Y, etc.) may comprise from around 0.0001 at. % to around 50 at. %); aluminum sulfate (Al(SO$_4$)$_3$) as well as sulfates of mixed metals that comprise at least about 50 at. % of Al relative to other metals (e.g., potassium aluminum sulfate, lithium aluminum sulfate; sodium aluminum sulfate, etc.; where, e.g., other metals (e.g., Na, K, Li, Mg, Ca, Sr, Ti, Fe, Si, Zn, La, Y, etc.) may comprise from around 0.0001 at. % to around 50 at. %); aluminum hydroxyphosphate sulfate as well as hydroxyphosphate sulfate of mixed metals that comprise at least about 50 at. % of Al relative to other metals (where, e.g., other metals (e.g., Na, K, Li, Mg, Ca, Sr, Ti, Fe, Si, Zn, La, Y, etc.) may comprise from around 0.0001 at. % to around 50 at. %), other aluminum salts and compounds and their various mixtures and combinations (including salts and compounds of other metals, such as Na or K or Li or Mg or Ca or Sr or Fe or Ti or Si or Zn or La or Y, etc.).

While Al-based adjuvants may be effective and not very harmful (e.g., compared to other heavy metals, such as other transition metals), the use of some of the alkaline and alkaline earth metals in adjuvant compositions in place of Al may enable further reduction in the probabilities of neurologic and autoimmune disorders, which is advantageous for public health.

In some designs, it may be advantageous for the nanofibers (or, in case of the composite nanofibers, at least for one or more of the components of the composite nanofibers) to comprise magnesium (Mg) atoms. In some designs, it may be advantageous for the amount of Mg to comprise about 2-100 at. % of all the metals in the nanofiber composition. Examples of such Mg-containing composition(s) of the nanofibers or nanofiber components may include, but are not limited to: various types (crystal structures) of magnesium oxide (MgO) including "doped" MgO (where Na or K or Li or Ca or Sr or other metals (e.g., Al or Fe or Ti or Si or Zn) may be present in addition to Mg in a relatively small content of less than around 10 at. %; in some designs from around 0.0001 at. % to around 1 at. %); magnesium hydroxide (Mg(OH)$_2$) as well as hydroxides of mixed metals that comprise at least about 50 at. % of Mg relative to other metals (e.g., where other metals may comprise from around 0.0001 at. % to around 50 at. %); magnesium oxyhydroxide as well as oxyhydroxides of mixed metals that comprise at least about 50 at. % of Mg relative to other metals (e.g., where other metals (e.g., Na or K or Li or Ca or Sr or Al or Fe or Ti or Si or Zn or their various combinations) may comprise from around 0.0001 at. % to around 50 at. %); magnesium phosphate (Mg$_3$(PO$_4$)$_2$ and various magnesium phosphate hydrates, such as monomagnesium phosphate (Mg(H$_2$PO$_4$)$_2$)·xH$_2$O, dimagnesium phosphate (MgHPO$_4$)·xH$_2$O, trimagnesium phosphate (Mg$_3$(PO$_4$)$_2$)·xH$_2$O) as well as phosphates of mixed metals that comprise at least about 50 at. % of Mg relative to other metals (e.g., where other metals (e.g., Na or K or Li or Ca or Sr or Al or Fe or Ti or Si or Zn or their various combinations) may comprise from around 0.0001 at. % to around 50 at. %); magnesium sulfate (MgSO$_4$) as well as sulfates of mixed metals that comprise at least about 50 at. % of Mg relative to other metals (e.g., where other metals (e.g., Na or K or Li or Ca or Sr or Al or Fe or Ti or Si or Zn or their various combinations) may comprise from around 0.0001 at. % to around 50 at. %); magnesium hydroxyphosphate sulfate, magnesium silicate, other magnesium salts and compounds and their various mixtures and combinations (including salts and compounds of other metals, such as Na or K or Li or Ca or Sr or Al or Fe or Ti or Si or Zn, etc.).

In some designs, it may be advantageous for the nanofibers (or, in case of the composite nanofibers, at least for one or more of the components of the composite nanofibers) to comprise calcium (Ca) atoms. In some designs, it may be advantageous for Ca to comprise about 2-100 at. % of all the metals in the nanofiber composition. Examples of such Ca-containing composition(s) of the nanofibers or nanofiber components may include, but are not limited to: various types (crystal structures) of calcium oxide (CaO) including "doped" CaO (where Na or K or Li or Mg or Sr or other metals (e.g., Fe or Ti or Al or Si or Zn or La or Y) may be present in addition to Ca in a relatively small content of less than around 10 at. %; in some designs from around 0.0001 at. % to around 1 at. %); calcium hydroxide (Ca(OH)$_2$) as well as hydroxides of mixed metals that comprise at least about 50 at. % of Ca relative to other metals (e.g., where other metals (e.g., Na or K or Li or Mg or Sr or Al or Fe or Ti or Si or Zn or La or Y or their various combinations) may comprise from around 0.0001 at. % to around 50 at. %); calcium oxyhydroxide as well as oxyhydroxides of mixed metals that comprise at least about 50 at. % of Ca relative to other metals (e.g., where other metals (e.g., Na or K or Li or Mg or Sr or Al or Fe or Ti or Si or Zn or La or Y or their various combinations) may comprise from around 0.0001 at. % to around 50 at. %); calcium phosphate (Ca$_3$(PO$_4$)$_2$ and various calcium phosphate hydrates, such as monocalcium phosphate (Ca(H$_2$PO$_4$)$_2$)·xH$_2$O, dicalcium phosphate (CaHPO$_4$)·xH$_2$O, tricalcium phosphate (Ca$_3$(PO$_4$)$_2$)·xH$_2$O) as well as phosphates of mixed metals that comprise at least about 50 at. % of Ca relative to other metals (e.g., where other metals (e.g., Na or K or Li or Mg or Sr or Al or Fe or Ti or Si or Zn or their various combinations) may comprise from around 0.0001 at. % to around 50 at. %); calcium sulfate (CaSO$_4$) as well as sulfates of mixed metals that comprise at least about 50 at. % of Ca relative to other metals (e.g., where other metals (e.g., Na or K or Li or Mg or Sr or Al or Fe or Ti or Si or Zn or La or Y or their various combinations) may comprise from around 0.0001 at. % to around 50 at. %); calcium hydroxyphosphate sulfate, calcium silicate, other calcium salts and compounds and their various mixtures and combinations (including salts of other metals, such as Na or K or Li or Mg or Sr or Al or Fe or Ti or Si or Zn or La or Y, etc.).

In some designs, it may be advantageous for the nanofibers (or, in case of the composite nanofibers, at least for the components of the nanofibers) to comprise at least a small fraction of lithium (Li) or potassium (K) or sodium (Na) atoms. In some designs, the atomic fraction of Li atoms (relative to other metal atoms in the composition of the nanofibers) may range from around 0.01 at. % to around 50.00 at. %. In some designs, the atomic fraction of K atoms (relative to other metal atoms in the composition of the nanofibers) may range from around 0.01 at. % to around 50.00 at. %.

In some designs, it may be advantageous to combine nanofibers of different compositions in a single formulation or application (e.g., have different subsets of the nanofibers with different atomic fraction of Al or Ti or Si or Fe or La or Y or Zn or Mg or Ca or Sr or Na or K or Li or other metals or utilize a mixture of oxides and hydroxides or sulfates or phosphates or silicates, etc.) in order to achieve a combination of more favorable properties (such as more enhanced immune response with reduced damages or unpleasant feelings in patients, among others).

In some designs, it may be advantageous for the nanofibers to comprise polymer(s). In some designs, such polymers may swell in contact with body fluids. In some designs, such polymer may (at least partially) gradually dissolve into body fluids over time (e.g., within, say, about 1-1,000 days). In some designs, such polymers may at least partially encase Al or Mg or Ti or Si or Fe or La or Y or Zn or Ca or Sr or Na or K or Li or La or Y or mixed metal oxides or silicates or salts in the nanofibers (e.g., in order to regulate the immune response or to reduce damage to the microvascular or other body components/parts or to provide other useful functions). In some designs, such polymers may act as a coating on the nanofibers. In some designs, such polymers may act as a pore filler arranged inside one or more pores of the nanofibers. In some designs, the weight fraction of the polymer(s) in the nanofibers may range from around 0.5 wt. % to around 95.0 wt. %. In some designs, such polymers may be deposited onto (or into) the nanofibers in a gaseous phase (e.g., by chemical vapor deposition (CVD) or atomic layer deposition (ALD) or other vapor deposition methods). In some designs, such polymers may be deposited into the nanofibers via solution deposition or solution infiltration methods. In some designs, the proper amount, deposition methodology and composition of the suitable polymers depend on a particular adjuvant application. Illustrative examples of suitable polymers may include, but are not limited to are chitosan, microspheres, collagen, gelatin, naturally occurring/derived polymers, starch, alginate, synthetic polymers, dextran, polystyrene, polyesters, amphiphilic block co-polymers, polyimides, polyanhydrides, monophosphoryl lipid A (MPL), among others and their combinations. In some designs, polymers may comprise amino acids. In some designs, polymers may comprise only amino acids (that is, be proteins).

In some designs, it may be advantageous for the nanofibers to exhibit a certain range of mechanical properties for most optimal performance as an adjuvant. In some designs, optimal values may depend on multiple parameters, including the size and shape of the nanofibers, the means of vaccination and other properties. In some designs, too weak or soft nanofibers may not be sufficiently effective, while too stiff or strong nanofibers may induce undesirable side effects. However, in some designs, such properties may preferably stay within certain ranges. For example, in some designs, it may be advantageous for the nanofibers to exhibit elastic modulus in the range from around 0.3 GPa to around 300.0 GPa. In some designs, it may be advantageous for the nanofibers to exhibit bending modulus (flexural modulus) in the range from around 0.3 GPa to around 300.0 GPa. In some designs, it may be advantageous for the nanofibers to exhibit flexural strength in the range from around 0.5 MPa to around 5 GPa. In some designs, it may be advantageous for the nanofibers to exhibit tensile strength in the range from around 10 MPa to around 30 GPa. In some designs, it may be advantageous for the nanofibers to exhibit bending fracture toughness in the range from around 0.05 MPa·m$^{1/2}$ to around 50 MPa·m$^{1/2}$. In some designs, it may be advantageous for the nanofibers to exhibit maximum elongation from around 1% to around 1,000%. Lower elastic modulus may be attained if the nanofibers comprise pores or softer (e.g., polymeric) materials, while higher elastic modulus could be attained for denser nanofibers composing metal oxides. Higher tensile strength and fracture toughness may be attained in nanofibers having smaller grain size (e.g., being amorphous), smaller diameter and smaller pore size and pore volume. Larger maximum elongation may be attained in polymer-comprising nanofibers and nanofibers comprising smaller grain size and having smaller diameter, smaller pore size, fewer (or no) slit-shaped pores (and more spherical or near-spherical pores) and fewer and smaller surface defects (to avoid fractures propagating from the surface or from the pores). In some designs, nanofibers may be composites comprising smaller nanofibers (in one example, organic polymer nanofibers comprising smaller inorganic nanofibers). Such smaller nanofibers may offer reinforcements of mechanical properties (e.g., strength, toughness, etc.) in addition to favorable biomedical response, which may be advantageous in some designs. Such composite nanofibers may be produced by electrospinning, for example.

In some designs, it may be advantageous for the nanofibers to exhibit a surface charge opposite to that of the proteins used in the vaccine formulations to facilitate their electrostatic interactions (adsorption). Most commonly, such proteins exhibit a negative surface charge (e.g., from around −2 mV to around −40 mV, when measured using Zeta-potential in the pH similar to that of the vaccine formulation, for example, around 7-8 pH). Therefore, in some designs, it may be advantageous for the nanofibers to exhibit a positive surface charge (e.g., from around +2.00 mV to around +80.00 mV, as measured using Zeta-potential at the same pH value, for example a pH of about 7-8). The surface charge on the surface of nanofibers may be controlled (tuned to the desired range) by introducing functional groups on the surface, by adsorption (or absorption) of ions, by the application of external electric field, by ion exchange, by depositing a positively charged material layer on their surface (e.g., about 0.2-10 nm), by using metal salts with mixed anions in the nanofiber formulation (e.g., aluminum hydroxyphosphate, $Al(OH)_x(PO_4)_y$,) and/or controlling the ratio of the anions (e.g., x:y in $Al(OH)_x(PO_4)_y$; where larger x may result in more positive charge) and other means.

In some designs, suitable techniques for synthesis of nanofibers may include catalyst-assisted chemical vapor deposition (CVD), cylindrical template-based synthesis, hydrothermal synthesis, electrospinning, formation of small rolls and others. For some applications, such techniques may suffer from high price and small yield. For some applications, some of such techniques may suffer from the formation of short nanofibers (e.g., below around 1-10 micron) or from relatively low aspect ratio (e.g., from around 2 to around 100) or from bridging and agglomeration or from inability to introduce internal pores or other shape or size or morphology limitations.

By contrast, in accordance with at least one embodiment of the disclosure, nanofibers produced by certain techniques may be particularly advantageous for use in the formation of suitable adjuvant compositions. Moreover, in some designs, it may be advantageous to incorporate nanofibers produced via different techniques into a vaccine adjuvant.

One exemplary technique for formation of nanofibers is via controlled oxidation of molted metal(s) or metal alloy(s). In one example, small metal oxide fibers may be produced by controlled oxidation of liquid aluminum or aluminum alloys or liquid magnesium or magnesium alloys (in some designs by using certain additives in these aluminum or magnesium alloys, such as vanadium, chromium, manganese, iron, cobalt, nickel, copper, zinc, selenium, sulfur, silicon, germanium, tellurium, cerium, praseodymium, neodymium, cerium, promethium, samarium, europium, gadolinium, gallium, terbium, dysprosium, holmium, erbium, thulium, ytterbium, among others). In some designs, the ceramic nanofibers produced by this technique may exhibit diameters in the range from around 3 nm to around 20 nm and a relatively high aspect ratio (e.g., in the range from around 50 to around 500,000). In some synthesis designs, the length of the ceramic (e.g., oxide) fibers produced by such a technique may exceed about 1 cm and in some cases may exceed even about 10 cm (in some special cases, the length may even exceed about 100 cm). Furthermore, in some designs, such nanofibers (e.g., aluminum oxide nanofibers) may be produced in bulk (as large blocks or aggregates) with overall volumes that may exceed 1 $cm^3$ or even about 1000 $cm^3$ or (in some cases) even about 1,000,000 $cm^3$. As such, in some designs, these bulk pieces of weakly bonded nanofibers may be broken apart and processed in order to produce a suitable suspension of nanofibers for adjuvant and other biomedical applications.

Another exemplary technique for formation of nanofibers may involve intermediate formation of small metal-organic nanofibers (e.g., metal alkoxide nanofibers, such as aluminum ethoxide or lithium-aluminum-ethoxide or aluminum-magnesium ethoxide or aluminum-magnesium-lithium ethoxide, magnesium ethoxide, magnesium iso-propoxide, magnesium n-propoxide, magnesium-calcium ethoxide, magnesium-calcium propoxide, calcium ethoxide, among others), which may be followed by their conversion into suitable metal oxide or metal salt nano fibers (such as metal oxide, metal hydroxide, metal oxyhydroxide, metal sulfate, metal carbide, metal phosphate, metal hydroxy phosphate, metal hydroxy phosphate sulfate, metal phosphate sulfate, metal hydroxy sulfate, metal carbonate, metal carbonate phosphate, etc.). In some designs, such intermediate formation of metal-organic nanofibers may be effectively used for the fabrication of porous metal oxide or metal salt nanofibers with controlled porosity and degree of crystallinity (such fibers could be made, for example, X-ray amorphous or be produced as polycrystalline with a controlled size of the crystalline grains). In an illustrative example, such a technique may involve (i) formation of suitable bimetallic alloy(s) (e.g., Al—Li, Mg—Li, Al—Mg—Li, Ca—Li, Ca—Mg—Li, Zn—Li, etc.) of suitable composition(s) (e.g., lithium-comprising metal alloys with Li content in the range from around 4 at. % to around 40 at. %), (ii) exposure of such bimetallic alloy(s) (e.g., in the form of microscopic or macroscopic particles or chunks or bulk pieces) to suitable solvent(s) (e.g., suitable alcohols such as ethanol, isopropanol, n-propanol, etc.) at the desired temperatures (e.g., from around 10° C. to around 120° C., depending on the recipe) in order to preferentially dissolve the more reactive metal (e.g., Li from the Al—Li or Mg—Li or Al—Mg—Li or Li—Ca or Li—Zn alloys, etc.) and simultaneously form small (nano-sized in diameter) metal-organic fibers of the less reactive metal(s) (e.g., Al or Mg or Ca or Zn or mixed metal alkoxides, such as ethoxide, isopropoxide, n-propoxide, methoxide and other related compounds) while reducing or preventing passivation of the less reactive metal (note that such an exposure may typically proceed from around 1 hour to around 100 days, depending on the particular chemistry, size of the alloy particles, temperature and other factors), (iii) drying and exposing the metal-organic nanofibers to an oxygen-comprising environment (e.g., dry air or wet air) to transform the organometallic nanofibers into oxide nanofibers (e.g., aluminum oxide (e.g., $Al_2O_3$) or magnesium oxide (e.g., MgO) or mixed aluminum-magnesium oxide or mixed aluminum-lithium oxide or aluminum-magnesium-lithium oxide or calcium oxide (e.g., CaO) or calcium-magnesium oxide (e.g., $CaMgO_2$) or zinc oxide (e.g., ZnO) or calcium zinc oxide (e.g., $CaZnO_2$) or other oxides, etc.), which may be porous. In some approaches, pre-dried metal-organic (e.g., alkoxide) nanofibers may be exposed to water vapors prior to transforming into oxides to better retain their shape and morphology. In some approaches, exposure metal-organic (e.g., alkoxide) nanofibers may be exposed to water vapors to form hydroxide or mixed hydroxide-alkoxide nanofibers. Such nanofibers may be further heated (e.g., either in oxygen containing environment or in an inert environment or vacuum at temperatures in the range from around 200 to around 1200° C., depending on the particular chemistry, exposure time, pressure and particular gaseous environment) to produce suitable oxide nanofibers, in some designs. In some designs, the heat-treatment time may range from around 1 sec (ultra-fast heating) to around 10 days (slow heating). Shorter time may typically require higher temperatures, while longer time may be needed for low-temperature heat-treatments. In some designs, hydroxide nanofibers may be heat-treated at low temperatures first to reduce their internal porosity prior to transformation to oxide nanofibers. In some designs, metal hydroxide or metal hydroxide-alkoxide or metal alkoxide nanofibers may be heated with other reactive gases or vapors or liquid reagents (e.g., at temperatures in the range from around 20 to around 1200° C.) to be transformed to metal salt (e.g., metal oxyhydroxide, metal sulfate, metal carbide, metal phosphate, metal hydroxy phosphate, metal hydroxy phosphate sulfate, metal phosphate sulfate, metal carbonate, metal carbonate phosphate, metal hydroxy sulfate, etc.) nanofibers. For example, reaction of sulfuric acid vapors (e.g., $H_2SO_4$) with metal hydroxide or hydroxy-alkoxide nanofibers may result with the formation of metal sulfate nanofibers. Reaction of phosphoric acid vapors ($H_3PO_4$) with metal hydroxide or hydroxy-alkoxide nanofibers may result with the formation of metal phosphate nanofibers. Other acids (silicic acid, carbonic acid, etc.), mixtures of acids as well as various sulfur oxides and other known active species may be used to transform metal hydroxide or metal hydroxide-alkoxide or metal alkoxide nanofibers to suitable metal salt nanofibers.

In some approaches, alkoxide (e.g., ethoxide or propoxide or n-propoxide, etc.) nanofibers may also be formed from alkoxide (e.g., ethoxide or propoxide or n-propoxide, etc.) powders via solution growth in an alcohol (e.g., ethanol or isopropanol or n-propanol, etc.) at elevated temperatures (e.g., about 50-200° C.).

In some synthesis approaches, the produced organometallic nanofibers may form agglomerates (bunches), which may be at least partially separated (exfoliated) into individual fibers by heat-treatment in a solvent (e.g., alcohol, such as ethanol, methanol, isopropanol, n-propanol, etc.) at temperatures in the range from around room temperature to around 200° C. (depending on a particular chemistry and solvent properties, including vaporization point and vapor pressure at different temperatures). In some designs, the produced small oxide fibers may comprise a significant amount of residual lithium (e.g., about 0.01-20 at. %), thus forming lithium-aluminum oxide or lithium magnesium oxide or lithium aluminum magnesium oxide or lithium zinc oxide or lithium calcium oxide, among other suitable compositions. In some synthesis designs, water or aqueous solutions of the desired pH (e.g., basic) may be used instead of the organic solvent(s) to form metal hydroxide, metal or metal oxide nanofibers. In some synthesis designs, the metal-organic nanofibers may be at least partially converted into hydroxide nanofibers prior to conversion into oxide (or other ceramic) fibers. In some designs, the ceramic (e.g., oxide) nanofibers may form large aggregates or blocks (bulk pieces) when separated from a solvent and dried.

In some designs, distinct structural features of the nanofibers may be produced via intermediate formation of metal-organic nanofibers (e.g., metal alkoxide nanofibers) is the ability to produce very long (e.g., about 5-500 micron) and very high aspect ratio (e.g., about 1:1000 or even more) amorphous or nanocrystalline nanofibers as well as the nanofibers with internal porosity and without any catalyst particles present. The distinct structural features of the metal-organic nanofibers (e.g., metal alkoxide nanofibers) produced by exposure of metals and metal alloys to the corresponding organic solvents (e.g., alcohols) include large length (e.g., about 5-500 micron) and very high aspect ratio (e.g., about 1:1000 or even more) metalorganic nanofibers without any catalyst particles present. Another feature is the diameter in the range from about 10 nm to around 500 nm. For some applications, detection of such distinct structural features in nanofibers may imply that such nanofibers were produced via transformation from metal-organic nanofibers.

Figure 2:
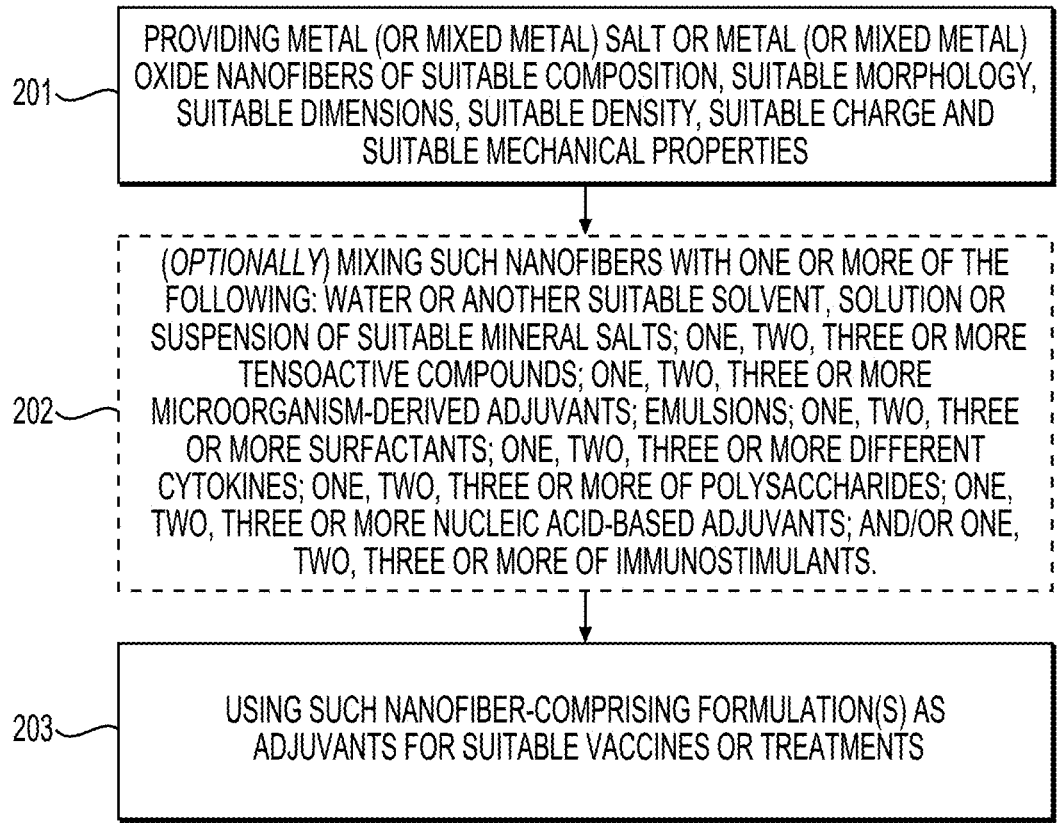
FIGS. 2-4 illustrate example methods that may be applied according to various embodiments.
Figure 3:
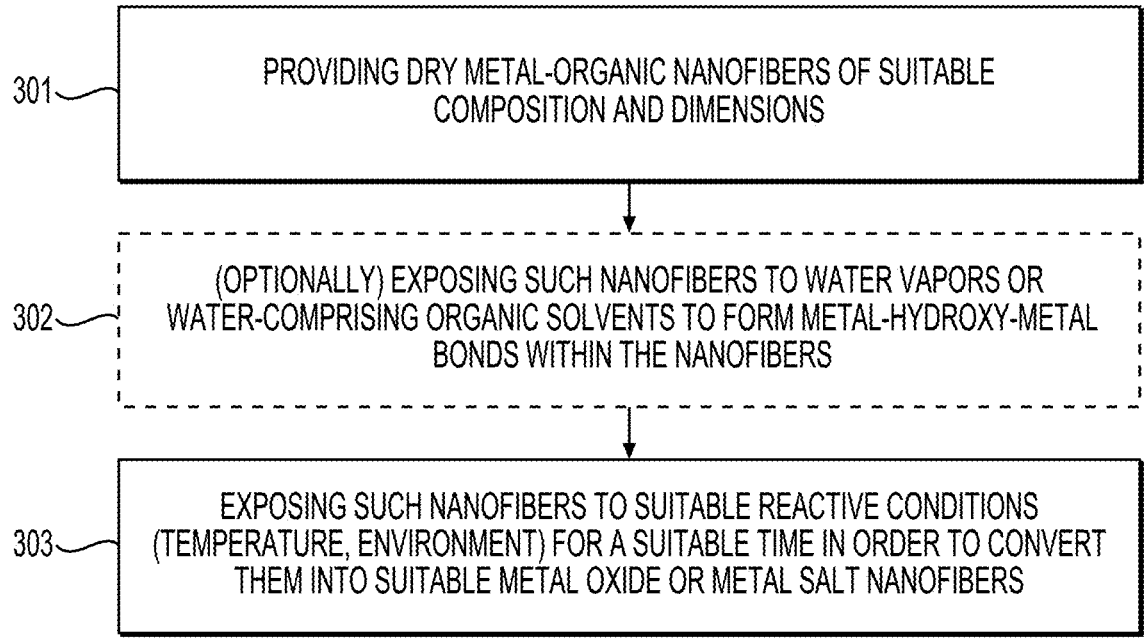

FIG. 2 illustrates an exemplary method for nanofiber-comprising formulation(s) as adjuvants for suitable vaccines or other suitable treatments, which comprises: (201) providing one or more nanofibers comprising metal (or mixed metal) salt or metal (or mixed metal) oxide of suitable composition (e.g., where one, two, three or more metals of the corresponding metal oxide or metal salts are selected from the group of Al, Ca, Mg, Li, Na, K, La, Y, Si, Fe and Zn and where a metal oxide or a metal salt is selected from one, two or more of the following: (i) metal oxide, (ii) metal hydroxide, (iii) metal oxyhydroxide, (iv) metal sulfate, (v) metal carbide, (vi) metal phosphate, (vii) metal hydroxy phosphate, (viii) metal hydroxy phosphate sulfate, (ix) metal phosphate sulfate, (x) metal hydroxy sulfate, (xi) metal carbonate, (xii) metal carbonate phosphate, (xiii) metal silicate), suitable dimensions (e.g., preferably nanofibers with diameters in the range from around 1 nm to around 500 nm, length in the range from around 250 nm to around 500 µm, an aspect ratios in the range from around 10 to around 100,000), suitable internal porosity (e.g., preferably having a total internal open pore volume in each nanofiber in the range from around 0.01 $cm^3/g$ to around 3 $cm^3/g$, and average pore size in the range from around 0.5 nm to around 50 nm; note that some or all of the fibers may be dense in some designs and comprise no pores), suitable density (e.g., preferably from around 0.3 to around 6 $g/cm^3$), suitable surface charge (e.g., preferably a positive surface charge from around +2.00 mV to around +80.00 mV, as measured using Zeta-potential at the pH value of about 7-8; note that some or all of the fibers may comprise surface charge outside this range and be even negative), suitable mechanical properties (e.g., preferably having elastic modulus in the range from around 0.3 GPa to around 300.0 GPa, bending modulus (flexural modulus) in the range from around 0.3 GPa to around 300.0 GPa, flexural strength in the range from around 0.5 MPa to around 5 GPa, tensile strength in the range from around 10 MPa to around 30 GPa, bending fracture toughness in the range from around 0.05 MPa·$m^{1/2}$ to around 50 MPa·$m^{1/2}$; note that some or all of the fibers may exhibit mechanical properties outside such a range); (202, optional) mixing such nanofibers with one or more of the following: water or another suitable solvent (e.g., oil); solution or suspension of suitable mineral salts; one, two, three or more tensoactive compounds; one, two, three or more microorganism-derived adjuvants; emulsions; one, two, three or more surfactants; one, two, three or more different cytokines; one, two, three or more of polysaccharides; one, two, three or more nucleic acid-based adjuvants; and/or one, two, three or more of immunostimulants; (203) using such nanofiber-comprising formulation(s) as adjuvants for suitable vaccines or treatments. FIG. 3 illustrates an exemplary method for the formation of metal oxide or metal salt nanofibers for suitable vaccines or other suitable treatments, comprising: (301) providing dry metal-organic (e.g., alkoxide) nanofibers of suitable composition (e.g., comprising one, two, three or more metals of the corresponding metal oxide or metal salts are selected from the group of Al, Ca, Mg, Li, Na, K, La, Y, Si, Fe and Zn) and dimensions (e.g., with diameters in the range from around 1 nm to around 500 nm, lengths in the range from around 250 nm to around 500 µm, aspect ratios in the range from around 10 to around 100,000, total internal open pore volumes in the range from around 0.01 $cm^3/g$ to around 3 $cm^3/g$, and average pore sizes in the range from around 0.5 nm to around 50 nm); (optional 302) exposing such nanofibers to water vapors or water-comprising organic solvents at suitable temperatures (e.g., from around 0° C. to around 400° C.) for a suitable time (e.g., from around 1 sec to around 100 hours) to form metal-hydroxy-metal bonds within the nanofibers; (303) exposing such nanofibers to suitable reactive conditions (e.g., temperature in the range from around 200° C. to around 1200° C.; pressure in the range from around 0.00001 atm. to around 10,000 atm.; suitable liquid or gaseous environment, for example, vacuum or oxygen-containing gases or sulfur or sulfur dioxide-containing gases or acids, etc.) for a suitable time (e.g., from around 1 sec to around 100 hours) in order to convert them into suitable metal oxide or metal salt nanofibers.

In some designs, an exemplary nanofiber may comprise Al between around 50 at. % to around 100 at. % of all the metals in a metal oxide or a metal salt of the nanofiber. In some designs, an exemplary nanofiber may comprise Ca between around 50 at. % to around 100 at. % of all the metals in the metal oxide or the metal salt of the nanofiber. In some designs, an exemplary nanofiber may comprise Mg between around 50 at. % to around 100 at. % of all the metals in the metal oxide or the metal salt of the nanofiber. In some designs, an exemplary nanofiber may comprise Zn between around 50 at. % to around 100 at. % of all the metals in the metal oxide or the metal salt of the nanofiber.

Figure 4:
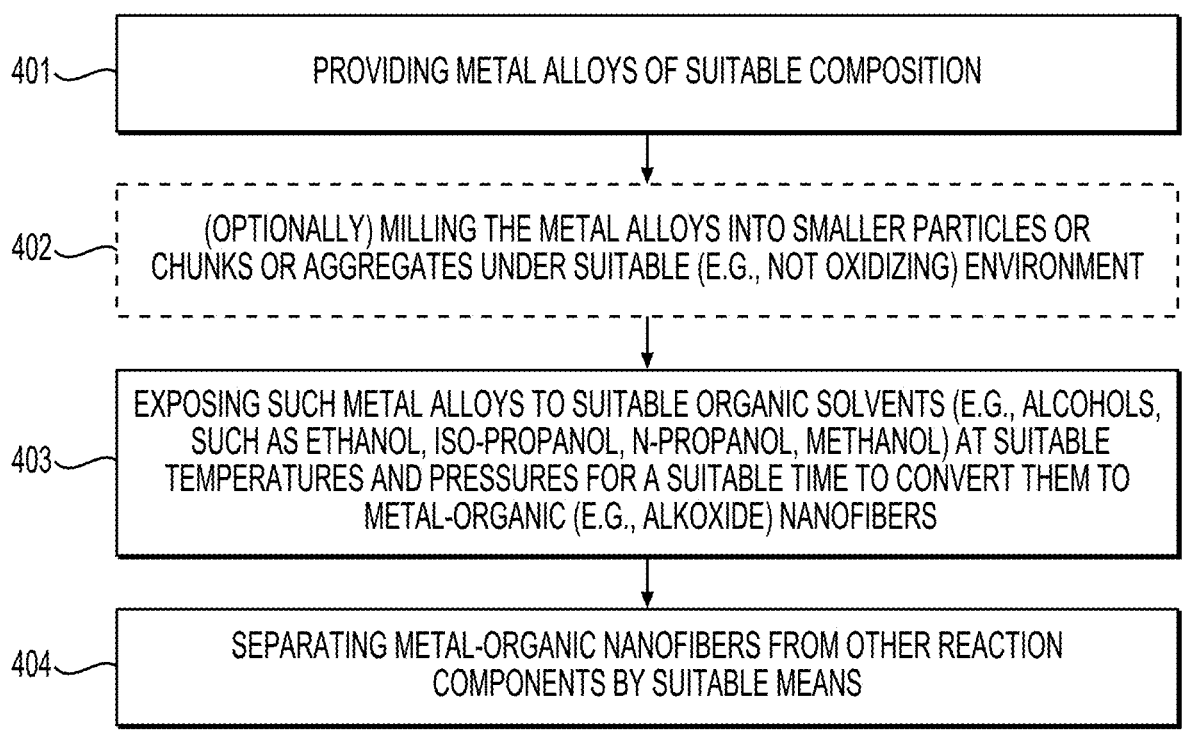

FIG. 4 illustrates an exemplary method for the formation of metal-organic (e.g., alkoxide) nanofibers, comprising: (401) producing or providing suitable metal alloy(s) (e.g., Al—Li, Mg—Li, Al—Mg—Li, Ca—Li, Ca—Mg—Li, Zn—Li, etc. with Li content in the range from around 4 at. % to around 40 at. %); (optional 402) milling the metal alloys into smaller particles or chunks or aggregates (e.g., with average dimensions in the range from around 5 micron to around 5 cm; in some designs—from around 20 micron to around 2 mm) under suitable (e.g., not oxidizing, nitrogen or argon or helium or vacuum) environment; (403) exposing such metal alloys to suitable organic solvents (e.g., alcohols, such as ethanol, iso-propanol, n-propanol, methanol, among others, depending on the alloy composition) at suitable temperatures (e.g., from around 10° C. to around 120° C.) and pressures (e.g., from around 0.0001 atm to around 10,000 atm.) for a suitable time (e.g., from around 10 min to around 100 days) to convert them to metal-organic (e.g., alkoxide) nanofibers; (404) separating metal-organic nanofibers from other reaction components by suitable means (e.g., centrifugation, filtration, drying, etc.).

Another favorable exemplary technique for formation of oxide or other nanofibers that also involve intermediate formation of metal-organic (precursor) nanofibers (e.g., alkoxide precursor fibers) in some applications is based on blow-spinning (e.g., melt spinning or solution spinning) of the organometallic (precursor) nanofibers and their subsequent transformation into hydroxide and oxide (or other compositions of) nanofibers (including porous fibers) by heat-treatment in a controlled gaseous environment (e.g., in wet or dry air or oxygen containing environment). In some designs, conversion to oxide (or other) nanofibers from the processor may take place during the blow-spinning when the process is conducted at elevated temperatures in a proper (e.g., oxygen containing) gaseous environment. In some designs, flame pyrolysis may be effectively utilized. In some designs, a polymer and/or other materials may be added into the blow-spinning precursor solution to control its viscosity, nanofiber morphology and/or porosity of the final product. In some designs, the polymer may be burned or oxidized or otherwise (at least partially) removed in the final product (nanofibers) (e.g., to induce porosity).

In some designs, the produced oxide nanofibers may be at least partially converted into hydroxide or oxyhydroxide nanofibers or nanofibers of other suitable composition(s) by known wet-chemistry treatment in an aqueous media or water-containing gas (e.g., air or nitrogen).

In some designs, a dispersion of nanofibers produced via the above-noted synthesis process (or by other suitable synthesis processes) may be formed by taking block(s) (or bundle(s) or aggregate(s)) of small ceramic fibers (or small or large flakes), adding a solvent (such as an alcohol or water or others), and then using physical agitation (e.g., milling, sonication, ultrasonication, various other mixing techniques, etc.) to break up the bundle to enable individual small ceramic fibers or flakes (or small bundles of less than about 10-20 fibers or flakes) to float freely in the solvent. In some designs, heating to elevated temperatures (e.g., about 50-200° C.) and exposing to elevated pressure (e.g., about 1-1000 atm.) may be utilized to break up the bundle to extract individual nanofibers. In some designs, surfactants may be added to achieve a better (e.g., more stable or comprising a larger portion of individual fibers or flakes) suspension.

In some designs, blocks (bulk pieces) of as-produced nanofibers may be physically or chemically attached to each other in a manner which is substantially weaker than the chemical bonds which form the atomic structure of the material into a fiber. In some designs, such weak bonds between individual fibers or flakes may be broken using an appropriate form of mechanical processing without significant breakage (or at least without excessive breakage) of the individual fibers. Examples of suitable mechanical processing may include but are not limited to: ball milling (including high impact or high energy ball milling), shaker milling, planetary milling, roller milling, agitator bead mills, sonication and ultrasonication. In some cases, the length of the as-produced individual nanofibers may be too long to form stable adjuvant suspensions (which may be desired in some designs) and thus require milling. In some designs, milling conditions (such as speed, media size or diameter, media mass, vessel geometry, type of milling, etc.) may affect dispersion characteristics (such as final aspect ratio and final size distribution of small fibers or their small bundles). In some process designs, a roller mill may be used to disperse a bulk of nanofibers to achieve final fiber aspect ratios. In some process designs, bulk nanofibers may be placed in a (e.g., cylindrical) vessel, along with milling media and a solvent. Various examples of the qualities of the milling media, solvent and milling conditions are described below. In some examples (e.g., particularly with respect to particles produced by oxidation of a metal or alloy melt), the milling media diameter may be selected in between around 0.01 cm and around 0.1 cm. In some examples, the milling media diameter may be selected in between around 0.1 cm and around 1 cm. In some examples, the milling media diameter may be selected in between around 1 cm and around 5 cm. In some designs, milling media of different sizes (e.g., diameters) and/or compositions may be combined to achieve the most desirable dispersion. In some designs, the optimal size (e.g., diameter) of the milling media may depend on the fiber dimensions and properties, speed of mechanical agitation, size of the vessel, density of the milling media and/or other conditions. For example, too small of a milling media diameter (e.g., below around 0.01 cm) may result in a heterogeneous mixture of nanofibers with a broad distribution of aspect ratios and/or bundles of nanofibers that are not fully separated and dispersed. On the other hand, if the milling media is too large in some applications, the resulting dispersion may comprise many bundles of large aspect ratio wires, as a media with a diameter much larger than the width of the nanowire may not be able to efficiently interact. In some process designs, it may be advantageous to combine multiple media sizes for the milling of the nanofibers and/or to use multiple milling stages with different sizes of media or, more broadly, different milling conditions (which may include using different solvents, different media, different milling energy and speed, etc.). In some designs, it may be advantageous to mill the ceramic (e.g., oxide) nanofibers (or flakes) via multiple stages with different types of agitation (e.g., a combination of different milling types or combine a milling and sonication (or ultrasonication) in a single stage or in multiple stages). In some designs, the solvent used in the milling process may be water. In some designs, the solvent used in the milling process may be an alcohol with a carbon chain size in the range of 1 and 5 carbons or in the range of 6 and 10 carbons. In some designs, the suitable milling media material may be yttria ($Y_2O_3$) stabilized zirconia oxide (YZT), corundum ($Al_2O_3$), steel, tungsten carbide, etc., to provide a few examples. In some designs, the milling media material may have a large effect on the properties of the dispersion. For example, if the media is not sufficiently dense, the media may not have enough inertia to break up and disperse large bundles of nanowires at a given milling speed. Conversely, if the milling media has a density greater than desired it may cause fracturing of the fibers (or flakes) perpendicular to their "long axis", resulting in the particles with an undesirably small aspect ratio.

In some designs, nanofiber-based (or nanofiber-containing) adjuvant formulations may advantageously comprise several components in various combination(s). Examples of such components may include but are not limited to: (i) various nanofibers of suitable morphology, composition and dimensions, (ii) various antigens; (iii) various delivery systems; (iv) various solution or suspension of mineral salts (which may not be in the shape of non-nanofibers); (v) various tensoactive compounds; (vi) microorganism-derived adjuvants; (vii) various emulsions; (viii) surfactants; (ix) various cytokines; (x) various polysaccharides; (xi) various nucleic acid-based adjuvants; and/or (xii) various immunostimulants. In a particular example, such component may include but are not limited to (i) a solution or suspension of mineral salts, (ii) one, two, three or more tensoactive compounds, (iii) one, two, three or more microorganism-derived adjuvants, (iv) one or more emulsions, (v) one, two, three or more surfactants, (vi) one, two, three or more different cytokines, (vii) one, two, three or more of polysaccharides, (viii) one, two, three or more nucleic acid-based adjuvants, (ix) one, two, three or more of immunostimulants, or (x) any combination thereof.

Suitable examples of antigens for nanofiber-based (or nanofiber-containing) adjuvant formulations may include, but are not limited to immunoglobulins (Ig), protein antigens, peptide antigens, HIV proteins, ovalbumin, albumin, viral antigens, tumor antigens, among others.

Suitable examples of mineral (inorganic) salts for nanofiber-based (or nanofiber-containing) adjuvant formulations may include but are not limited to aluminum oxide, aluminum salts (including, but not limited to aluminum hydroxide, aluminum oxyhydroxide, aluminum phosphate, aluminum hydroxycarbonate, aluminum sulfate, their various mixtures, etc.), salts of calcium (including, but not limited to calcium oxide, calcium hydroxide, calcium oxyhydroxide, calcium phosphate, calcium hydroxycarbonate, calcium sulfate, their various mixtures, etc.), salts of magnesium (including, but not limited to magnesium oxide, magnesium hydroxide, magnesium oxyhydroxide, magnesium phosphate, magnesium hydroxycarbonate, magnesium sulfate, their various mixtures, etc.), salts of potassium (including, but not limited to potassium oxide, potassium hydroxide, potassium oxyhydroxide, potassium phosphate, potassium hydroxycarbonate, potassium sulfate, their various mixtures, etc.), salts of sodium (including, but not limited to sodium oxide, sodium hydroxide, sodium oxyhydroxide, sodium phosphate, sodium hydroxycarbonate, sodium sulfate, their various mixtures, etc.), iron oxide and other mineral salts of iron, yttrium oxide or other mineral salts of yttrium, lanthanum oxide or other mineral salts of lanthanum, zirconium oxide and other mineral salts of zirconium, zinc oxide and other mineral salts of zinc or their various mixtures, composites and combinations.

Suitable examples of tensoactive compounds for nanofiber-based (or nanofiber-containing) adjuvant formulations may include but are not limited to Quil A or other components of saponin, tenso-active glycosides, others and their various mixtures and combinations.

Suitable examples of microorganism-derived adjuvants for nanofiber-based (or nanofiber-containing) adjuvant formulations may include but are not limited to Coley's toxins, Cholera toxin, CpG DNA vaccine adjuvant, MPL adjuvant, Cholera toxin B subunit, LTR192G vaccine adjuvant, *Bordetella pertussis* component vaccine adjuvant, *E. coli* heat-labile toxin LT, CTA1-TT gene fusion protein, Etx B subunit adjuvant, killer *Corynebacterium parvum* vaccine adjuvant, lipopolysaccharide vaccine adjuvant, LTK63 vaccine mutant adjuvant, lipopolysaccharide vaccine adjuvant, LTK63 vaccine adjuvant mutant, *Corynebacterium*-derived P40 vaccine adjuvant, Flagellin vaccine adjuvant, LTK72 vaccine adjuvant, MPL-SE vaccine adjuvant, non-toxic mutant E-112K of Cholera toxin mCT-E112K, Ty particles vaccine adjuvant, components of bacteria cell walls, Complete Freund's adjuvant, among others.

Suitable examples of emulsions for nanofiber-based (or nanofiber-containing) adjuvant formulations may include but are not limited to water-in-oil and oil-in-water emulsions, based on squalene ($C_{30}H_{50}$), mono- and diglycerides of fatty acids, polysorbate-20, diglyceride, fatty acid ester, cetostearyl alcohol, isopropyl myristate, monophosphoryl lipid A, montanide, incomplete Freund's adjuvant, adjuvant 65, MF59, among others.

Suitable examples of surfactants for nanofiber-based (or nanofiber-containing) adjuvant formulations may include but are not limited to anionic surfactants, such as sodium dodecylbenzene sulphonate (SDBS), sodium dodecyl sulphate (SDS), ammonium lauryl sulphate, potassium lauryl sulphate, sodium stearate, cationic surfactants, cetyl trimethyl ammonium bromide (CTAB), benzalkonium chloride, cetrimonium chloride, distearyl dimethylammonium chloride, non-ionic surfactants, such as gum arabic (GA), polyoxyethylene (10) nonylphenyl ether, poly vinyl pyrrolidone (PVP), tween 80, tween X-100, stearyl alcohol, oleic acid, oleyl amine, rokanol K7, rokacet O7, amphoteric surfactants, such as lecithin, sodium lauroamphoacetate, hydroxysultaine, cocamidopropyl betaine, other and other various combinations.

Suitable examples of cytokines for nanofiber-based (or nanofiber-containing) adjuvant formulations may include but are not limited to interferon-gamma (IFN-γ), tumor necrosis factor-alpha (TNF-α), interleukins (IL), IL-1, IL-2, IL-6, IL-12, IL-15, IL-18, IL-21, IL-12p70, interferon-alpha (IFN-α), interferon-gamma (IFN-γ), granulocyte/macrophage colony stimulating factor (GM-CSF), chemokine, others and their various combinations.

Suitable examples of polysaccharides for nanofiber-based (or nanofiber-containing) adjuvant formulations may include but are not limited to lipopolysaccharides, chitosan-based nanoparticles (NPs), glucan, mannose, insulin polysaccharide, Chinese medicinal herb polysaccharide, among others and their various combinations.

Suitable examples of nucleic acid-based adjuvants for nanofiber-based (or nanofiber-containing) adjuvant formulations may include but are not limited to synthetic analogues of double-stranded RNA, such as viral ds RNA, and molecular mimics of single-stranded RNA, such as imidazoquinolines, synthetic analogues of single-stranded DNA in the form of oligodeoxynucleotides (ODNs) containing one or more unmethylated CpG motifs, among others and their various combinations.

Suitable examples of delivery systems for nanofiber-based (or nanofiber-containing) adjuvant formulations may include but are not limited to liposomes, pH-sensitive liposomes, cationic liposomes, long-circulating immunoliposomes, liposomes covered in an envelope of glycoprotein of a virus (virosome), virus-like particles, nanoparticles made of viral proteins, such as phospholipids and influenza hemagglutinin, biodegradable polymer microspheres, immune stimulating complexes (ISCOMs, such as ISCOMATRIX™), Quil A, QS21, chitosan, microspheres, gelatin, naturally occurring/derived polymers, starch, alginate, synthetic polymers, dextran, polystyrene, polyesters, amphiphilic block co-polymers, polyimides, polyanhydrides, monophosphoryl lipid A (MPL), among others and their various combinations.

Suitable examples of immunostimulants for nanofiber-based (or nanofiber-containing) adjuvant formulations may include but are not limited to bacterial lipopeptide, lipoprotein, and lipoteichoic acid; mycobacterial lipoglycan; yeast zymosan, poria, viral double-stranded RNA, lipopolysaccharide, lipid A, monophosphotyl lipid A (MPL®), AGPs, GLA, flagellin, viral single stranded RNA, imidazoquinolines, bacterial DNA, CpG DNA, hemozoin, uropathogenic bacteria, protozoan profilin, saponins (Quil-A, QS-21, tomatine, ISCOM, ISCOMATRIX), cytokines: GM-CSF, IL-2, IFN-γ, Flt-3, bacterial toxins (CT, LT), among others and their various combinations.

In some embodiments of the present disclosure, nanofiber-based adjuvants formulations may be delivered to a body via intramuscular, intradermal, nasal, sublingual, buccal, oral, rectal, vaginal, transcutaneous, subcutaneous, intravenous, epidural, intrathecal, respiratory and/or urogenital routes, among others. In some embodiments, mucosal delivery of nanofiber-based adjuvants formulations may favor the induction of nasal, oral, rectal, vaginal, respiratory or urogenital tract immune responses. In some embodiments, mucosal delivery of nanofiber-based adjuvants formulations may favor the immunization of the adjacent mucosal site or specifically interconnected inductive-expression mucosal systems.

In some embodiments, described above or other nanofiber-based adjuvants formulations may be advantageously used in live or killed whole virus vaccines and attenuated virus vaccines.

In some embodiments, described above or other nanofiber-based adjuvants formulations may be advantageously used in subunit vaccines. Examples of subunit vaccines comprise viral surface proteins, immunogenic virus-like nanoparticles, and receptor bonding domains of proteins.

In some embodiments, described above or other nanofiber-based adjuvants formulations may be advantageously used in nucleic acid vaccine platforms. Examples of nucleic acid vaccine platforms comprise RNA, mRNA and DNA.

In some embodiments, described above or other nanofiber-based adjuvants formulations may be advantageously used in COVID-19 vaccine, SARS strains vaccine, SARS-CoV-1, SARS-CoV-2 and other coronaviruses (CoVs) strains vaccines. Examples of such vaccines may include but are not limited to: viral spike S protein, including its different forms and variants, m-RNA vaccine encoding proteins, including S proteins, adenovirus type 5 vector that expresses S protein, recombinant proteins, live attenuated virus, inactivated virus, non-replicating and replicating viral vectors, COVID virus-like particles, SARS virus-like particles, nucleic acids (RNA, DNA), and other viral peptides, polypeptides and proteins.

In some embodiments, above-described or other nanofiber-based adjuvants formulations may be advantageously used in vaccines for protection against or even prevention of a broad range of diseases, such as (but not limited to): malaria, adenovirus, anthrax, cholera, diphtheria, hepatitis A, hepatitis B, human immunodeficiency viruses (HIV) that may cause acquired immunodeficiency syndrome (AIDS), Haemophilius influenza type b, human papilloma virus (HPV), seasonal influenza (Flu), Japanese Encephalitis, measles, meningococcal, mumps, pertussis, pneumococcal, polio, rabies, rotavirus, rubella, shingles, smallpox, tetanus, tuberculosis, varicella, yellow fewer, various coronaviruses (e.g., 229E (alpha), NL63 (alpha), OC43 (beta), HKU1 (beta), MERS-CoV, a beta virus that may cause Middle East respiratory syndrome (MERS), SARS-CoV, a beta virus that may cause severe acute respiratory syndrome (SARS), SARS-CoV-2, which may cause COVID-19, among others) and/or other diseases and their various combinations.

Interestingly, in addition to the use of the described above or other nanofibers (with properties and composition as described above, including those that are produced by the described above synthesis methods) as vaccine adjuvants or components of vaccine adjuvants, similar or the same nanofibers may also be advantageously used in other medical and biomedical applications where nanofibers exhibit a direct contact with body fluids. Note that in some designs, other (e.g., not adjuvant) applications may benefit from slightly different nanofiber properties.

In some embodiments, nanofibers or nanofiber-based adjuvant formulations as described above or other nanofibers or nanofiber-based adjuvant formulations may also be advantageously used to mediate vaccine-induced immune response to combat non-invasive and invasive bacteria, and viruses or other infectious diseases. For example, such nanofibers or nanofiber-based adjuvants formulations may be delivered via mucosal or other suitable delivery routes to treat *Helocobacter pylori*, *Vibrio cholerae*, enterotoxigenic *Escherichia coli* (ETEC), *Shigella* spp., *Clostridium difficile*, rotaviruses, calici viruses, among other bacteria and viruses. In another example, such nanofibers and nanofiber-based adjuvants formulations may be delivered via mucosal or other suitable delivery routes to treat respiratory infections caused by *Mycoplasma pneumoniae*, influenza viruses, respiratory syncytial virus, various coronaviruses (e.g., COVID-19) among other bacteria and viruses. In yet another example, such nanofibers or nanofiber-based adjuvants formulations may be delivered via mucosal or other suitable delivery routes to treat sexually transmitted infections caused by, for example, HIV, *Chlamidia trahomatis, Neiseria gonorrhoeae*, herpes simplex virus and other bacteria and viruses.

In other embodiments, nanofibers or nanofiber-based adjuvant formulations as described above or other nanofibers or nanofiber-based adjuvants formulations may be advantageously used to mediate vaccine-induced immune response(s) for preventing or possibly treating of autoimmune illnesses. In one example, such nanofibers or nanofiber-based adjuvants formulations may be delivered to treat autoimmune arthritis, type I diabetes, experimental autoimmune encephalitis, myasthenia gravis, autoimmune ear chondritis, autoimmune uveitis, autoimmune thyroiditis, multiple sclerosis, Behcet disease and autoimmune eye disease, among others.

In other embodiments, nanofibers or nanofiber-based adjuvant formulations as described above or other nanofibers or nanofiber-based adjuvants formulations may be advantageously used to mediate vaccine-induced immune response for preventing or possibly treating of allergic disorders, such as allergic rhinitis, asthma, hypersensitivity response to airborne allergens such as pollens, dust mites, spores, *Parietaria*, animal dander, among other allergic disorders.

In other embodiments, nanofibers or nanofiber-based adjuvant formulations as described above or other nanofibers or nanofiber-based adjuvants formulations may also be advantageously used to mediate vaccine-induced immune response for preventing or possibly treating of cancer diseases, such as non-small cell lung cancer, prostate cancer, melanoma, cervical cancer, breast cancer, glioblastoma, non-Hodgkin lymphoma, pancreatic cancer, brain cancer, liver cancer, colon cancer, ovary cancer, lung cancer, among other cancers.

In other embodiments, nanofibers or nanofiber-based adjuvant formulations as described above or other nanofibers or nanofiber-based adjuvants formulations may also be advantageously used in combination with anti-cancer drugs or cancer immunotherapy agents to mediate vaccine-induced immune response and to enhance anti-tumor immune response for preventing or possibly treating of cancers diseases, such as non-small cell lung cancer, prostate cancer, melanoma, cervical cancer, breast cancer, glioblastoma, non-Hodgkin lymphoma, pancreatic cancer, brain cancer, liver cancer, colon cancer, ovary cancer, lung cancer, among other cancers.

In other embodiments, nanofibers or nanofiber-based adjuvant formulations as described above or other nanofibers or nanofiber-based adjuvants formulations (in some designs with other adjuvants or additives) may be advantageously used with local anesthetics to synergistically prolong the duration of sensory-motor block and limit a cumulative dose requirement. In this case, harmful effects of general anesthetics could be minimized or prevented. Similarly, harmful effects of local anesthetics could be reduced (e.g., since the dose may be reduced for the same effect). In some embodiments, the time needed for anesthetic onset may also be reduced and the duration of the anesthetic (before additional dosing is needed) may be increased.

Examples of suitable local anaesthetics may include, but are not limited to benzocaine, chloroprocaine, cocaine, cyclomethycaine, dimethocaine, piperocaine, propoxycaine, procaine, proparacaine, tetracaine, articaine, bupivacaine, cinchocaine, levobupivacaine, lidocaine, mepivacaine, prilocaine, ropivacaine, trimecaine, saxitoxin, neosaxitoxin, tetrodotoxin, menthol, eugenol, spilanthol, iontocaine, septocaine, benzocaine, chloroprocaine, cyclomethycaine, dimethocaine/larocaine, piperocaine, propoxycaine, procaine/novocaine, etidocaine, others and their various combinations. Examples of suitable other adjuvants or additives (to be used in combination with nanofibers and nanofiber-based adjuvants) may include but are not limited to opioids, morphine, fentanyl, sufentanil, hydromorphone, buprenorphine, tramadol, clonidine, dexmedetomidine, dexamethasone, midazolam, neostigmine, ketamine, epinephrine, alpha-2 adrenergic antagonists, steroids, anti-inflammatory drugs, magnesium sulfate, others and their various combinations.

In some embodiments, nanofibers or nanofiber-based adjuvants may be combined with other adjuvants in anesthetics such as epinephrine, clonidine, dexmedetomidine, adenosine, sodium bicarbonate, hyaluronidase, and others. This may be advantageous as mechanisms such as vasoconstriction, pH adjustment, and/or others may improve the efficacy of administered anesthetics.

In other embodiments, nanofibers or nanofiber-based adjuvant formulations as described above or other nanofibers or nanofiber-based adjuvants formulations (in some designs, with other adjuvants or additives) may also be advantageously used in combination with analgesics for pain management. Illustrative examples of suitable analgesics may include but are not limited to: acetaminophen, non-steroidal anti-inflammatory drugs, COX-2 inhibitors, opioids, morphine, codeine, oxycodone, hydrocodone, dihydromorphine, pethidine, cannabis, aspirin, ibuprofen, naproxen, codeine, hydroxyzine, promethazine, carisoprodol, tripelennamine, nefopam, orphenadrine, pregabalin, gabapentin, cyclobenzaprine, hyoscine, methylphenidate, caffeine, ephedrine, dextroamphetamine, methamphetamine, cocaine, carbamazepine, gabapentin, pregabalin, their various combinations, among others.

In other embodiments, nanofibers or nanofiber-based adjuvant formulations as described above or other nanofibers or nanofiber-based adjuvants formulations (in some designs, with other adjuvants or additives) may also be advantageously used in combination with analgesic pain management, such as antidepressants, tricyclic anti-depressants, amitriptyline, such as nortriptyline, desipramine, serotonin and noradrenaline reuptake inhibitors, such as duloxetine, venlafaxine, selective serotonin reuptake inhibitors, such as paroxetine and fluoxetine, anticonvulsants, such as gabapentin, carbamazepine, oxcarbazepine, lamotrigine, and pregabalin, alpha-2-adrenergic agonists, such as clonidine and tizanidine, corticosteroids, local anesthetics, such as lidocaine, topical agents, such as capsaicin, N-methyl-D-aspartate (NMDA) antagonists, cannabinoids, such as delta(9)-trans-tetrahydrocannabinol, bisphosphonates, such as zoledronate and ibandronate, and calcitonin, gamma-amino-butyric acid agonists, such as baclofen, neuroimmunomodulatory agents, such as thalidomide, and others.

In other embodiments, nanofibers or nanofiber-based adjuvant formulations as described above or other nanofibers or nanofiber-based adjuvants formulations (in some designs, with other adjuvants or additives) may also be advantageously used in combination with antiseptic agents to combat bacteria or virus growth. Illustrative examples of suitable antiseptic agents may include but not limited to ethanol, iso-propanol, formaldehyde, glutaraldehyde, chlorhexidine digluconate, triclosan, propamidine, sodium hypochlorite, iodine, silver nitrate, thiomersal, hydrogen peroxide, peracetic acid, phenol, o-phenylphenol, benzalkonium chloride, metronidazole, daptomycin, vancomycin, tobramycin, amikacin, and other aminoglycosides, mupirocin, polymyxin, nitrofurantoin, methenamine, copper or copper oxide nanoparticles, silver or silver oxide nanoparticles, gold nanoparticles, zinc oxide nanoparticles, calcium oxide or hydroxide nanoparticles, magnesium oxide or hydroxide nanoparticles, iron oxide or hydroxide nanoparticles, yttrium oxide nanoparticles, titanium oxide nanoparticles, others and their various combinations. In some designs, antiseptic agents may be incorporated into the pores or on the surface of nanofibers.

In other embodiments, nanofibers or nanofiber-based adjuvant formulations as described above or other nanofibers or nanofiber-based adjuvants formulations may be advantageously used in combination with reversal agents. In some designs, this may be beneficial because using nanofibers may localize the area affected by the reversal agent, reduce the dosage needed for the reversal, or increase the duration of effective reversal attributes. Illustrative examples of suitable reversing muscle relaxants include but are not limited to neostigmine and others, benzodiazepines with flumazenil and others, opioids with naloxone and others, neuromuscular-blocking drugs with sugammadex and others.

In some embodiments, it may be beneficial to use nanofibers or nanofiber-based adjuvant formulations as described above or other nanofibers or nanofiber-based adjuvants with inhalants, either as drug delivery devices, bulking agents, suspension stabilizers, surfactants, or dispersing agents. In some cases, nanofibers may help to distribute medicines throughout the lungs. In some designs, the pharmaceutical ingredient may be bound to the nanofiber surface molecularly or macroscopically with the use of a binder. By being bound to the adjuvant, less of the pharmaceutical ingredient(s) may be needed in some designs, both in single doses, and over time (e.g., each successive dose may last longer). In some embodiments, nanofiber adjuvants may be used in conjunction with inhalation treatment of terminal (or non-terminal) respiratory illness. In some designs, this may include treating chronic respiratory diseases such as asthma, chronic obstructive pulmonary disease, acute respiratory distress syndrome and others, restrictive lung diseases, such as pneumoconiosis, radiation fibrosis, hypersensitivity pneumonitis, tuberculosis, and others, upper respiratory tract infections such as sinusitis, tonsillitis, otitis media, pharyngitis, laryngitis, and others, lower respiratory tract infections such as pneumonia, acute respiratory syndrome, pneumocystis pneumonia, community acquired, healthcare-associated, hospital-acquired, and ventilator-acquired pneumonia, lung abscesses, and others, tumors such as such as small cell lung cancer, non-small cell lung cancer (e.g. adenocarcinoma, squamous cell carcinoma, large cell lung carcinoma) carcinoid, Kaposi's sarcoma, melanomas, lymphomas, pleural mesothelioma, pulmonary hamartoma, congenital malformations, and others.

In other embodiments, nanofibers or nanofiber-based adjuvant formulations as described above or other nanofibers or nanofiber-based formulations (in some designs, with other additives) may be advantageously used as scaffolds to stimulate in-vitro or in-vivo growth of nerves, axons, dendrites and/or stroma.

In some designs, such scaffolds may be "living" scaffolds which are regenerative scaffolds comprised of living neural cells (which may be the patient's own cells, in some designs) in a preformed porous nanofiber-comprising three-dimensional (3-D) architecture, where the pore size and pore shape may be controlled by the spacing between the nanofibers.

In some designs, the nanofibers in the scaffold may be bonded with synthetic or naturally derived polymers (e.g., natural polymers, including proteins, such as collagen tissue) and other suitable tissue-engineered biosynthetic matrices to maintain the desired scaffold shape. In some designs, the tissue-engineered biosynthetic matrix materials may include synthetic or naturally derived amphiphilic polymers. In some designs, the tissue-engineered biosynthetic matrix materials may include synthetic or naturally derived hydrophilic polymers. In some designs, the tissue-engineered biosynthetic matrix materials may include synthetic or naturally derived hydrophobic polymers.

In some designs, the nanofibers in the scaffold may be aligned along a direction to stimulate the growth of nerves, axons, dendrites and stroma along such directions. In some designs, nanofibers mixed with the proteins (e.g., collagen) may be electrospun to produce a scaffold. Placing the oriented nanofiber-comprising scaffold along the desired (e.g., previously broken) pathway between the areas of healthy nerve cells may facilitate the axon growth and cell migration eventually connecting the areas of nerves and, for example, repairing the previously broken nervous pathway.

For example, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used as scaffolds to stimulate the growth of neurons in a central nervous system. In another related embodiment, nanofibers or nanofiber-based adjuvant formulations as described above or other nanofibers and nanofiber-based formulations may be advantageously used as scaffolds to stimulate growth of neurons in peripheral nervous system. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used as nerve allograft. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may also be advantageously used to regain nerve functions. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may also be advantageously used to restore connections between spinal nerves and a spinal cord. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to regain the growth of blood vessels, bundles of neurons, epineurium, perineurium, and/or fascicles in a spinal nerve. In another related embodiment, nanofibers or nanofiber-based adjuvant formulations as described above or other nanofiber-based adjuvants formulations (including those where nanofibers are bonded with natural polymers, such as collagen, or other known or suitable tissue-engineered biosynthetic matrix materials) may also be advantageously used to regain the growth of endoneurium, Schwann cells, myelinated neurons, and/or unmyelinated neurons in a spinal nerve. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to assist Schwann cells in regeneration of neurons. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to regenerate axons. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to treat neurapraxia (demyelination), myelin sheath compression, radial nerve compression, axonotmesis and/or neurotmesis. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used as nerve allograft. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may also be advantageously used to regain nerve functions. In another related embodiment, nanofibers or nanofiber-based adjuvant formulations as described above or other nanofiber-based adjuvants formulations (including those where nanofibers are bonded with natural polymers, such as collagen, or other known or suitable tissue-engineered biosynthetic matrix materials) may be advantageously used to gain unidirectional nerve growth. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to gain multidirectional nerve growth.

In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used as a scaffold to stimulate in-vitro or in-vivo growth of corneal epithelium. In some designs, it may be advantageous for nanofibers or nanofiber-based formulations to be confined within tissue-engineered biosynthetic matrices with optical clarity, curvature and/or biomechanical properties tuned to favorably influence cellular growth and behavior of corneal epithelium. Illustrative examples of such tissue-engineered biosynthetic matrices may include but are not limited to collagen tissue, synthetic or naturally derived amphiphilic polymers, synthetic or naturally derived hydrophilic polymers, or synthetic or naturally derived hydrophobic polymers, among others.

In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to control the growth of lymph vessels (lymphangiogenesis). In some designs, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may exhibit high strength and stiffness, which may be desired to accommodate high stresses and provide a stable support for the lymphatic cells to migrate and proliferate. In some designs, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may exhibit necessary chemical structure and surface modifications to affect growth or inhibition of lymphatic endothelial and muscle cells. In one example, nanofibers or nanofiber-based adjuvant formulations as described above or other nanofibers and nanofiber-based adjuvants formulations may assist lymphatic system to attract immune cells between the inflammation sites and lymph nodes and in draining of the interstitial fluid. In another example, nanofibers or nanofiber-based adjuvant formulations as described above or other nanofibers and nanofiber-based adjuvant formulations may mediate vaccine-induced immune response to treat conditions like lymphedema. In yet another example, nanofibers or nanofiber-based adjuvant formulations as described above or other nanofibers and nanofiber-based adjuvants formulations may inhibit the growth of lymphatic vessels to prevent cancer evolution or organ transplantation lymphangiogenesis.

In another related embodiment, nanofibers or nanofiber-based adjuvant formulations as described above or other nanofibers or nanofiber-based formulations (including those where nanofibers are bonded with natural polymers, such as collagen, or other known or suitable tissue-engineered biosynthetic matrix materials) may be advantageously used for revascularization. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to stimulate muscle fibers regrowth. In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used to regain muscle functions. In another embodiment, nanofibers or nanofiber-based adjuvant formulations as described above or other nanofibers and nanofiber-based formulations may be advantageously used for restoring blood pressure. In another embodiment, nanofibers or nanofiber-based adjuvant formulations as described above or other nanofibers and nanofiber-based formulations may be advantageously used to restoring paralysis.

In another related embodiment, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may be advantageously used for wound healing. In some designs, nanofibers or nanofiber-based adjuvant formulations as described above or other nanofibers and nanofiber-based formulations (including those where nanofibers are bonded with natural polymers, such as collagen, or other known or suitable tissue-engineered biosynthetic matrix materials) may provide a stable support for the migration of red blood cells to produce a clog in the wound and enable hemostasis. To achieve such a goal, the nanofibers (which may be bonded with natural polymers, such as collagen, or other known or suitable tissue-engineered biosynthetic matrix materials) may be brought into direct contact with the wound to accelerate the healing process. In some designs, nanofibers (which may be bonded with natural polymers, such as collagen, or other known or suitable tissue-engineered biosynthetic matrix materials) may be attached to a sterile fabric (e.g., part of the bondage) to be applied to the wound. In some designs, the pores in the porous nanofibers may be advantageously filled with nanoparticles of silver (Ag) or salts of silver that may serve as anti-bacterial agents. In another related embodiment, nanofibers or nanofiber-based adjuvant formulations as described above or other nanofibers and nanofiber-based adjuvant formulations may be used to mediate vaccine-induced immune response to initiate the migration of white blood cells in the wound area and their differentiation and engulfment of bacteria to subside the inflammation. In another related embodiment, nanofibers or nanofiber-based adjuvant formulations as described above or other nanofibers and nanofiber-based adjuvants formulations may be used to mediate revascularization, reforming of capillaries, and/or granulation tissue formation, migration and proliferation of fibroblasts and myofibroblasts. In another related embodiment, nanofibers or nanofiber-based adjuvant formulations as described above or other nanofibers and nanofiber-based adjuvants formulations may be used to mediate the locomotion of epithelial cells, transition from granulation tissue to scar tissue, reorganization and/or maturation of collagen fibers to increase or maximize tensile strength. In some designs, nanofibers (which may be bonded with natural polymers, such as collagen, or other known or suitable tissue-engineered biosynthetic matrix materials) may be attached to a sterile fabric (e.g., part of the bondage) to be applied to the affected area.

In some designs, nanofiber-based (or nanofiber-containing) formulations may beneficially be used in the form of porous scaffolds, porous membranes, fibers, braided sutures or other supports with superior thermal, mechanical, chemical, and physical properties for a broad range of biomedical applications. In some designs, the nanofiber-based (or nanofiber-containing) porous scaffolds, porous membranes, fibers, braided sutures or other supports may only comprise inorganic materials (for example, in the form of the oxides). In some designs, the nanofibers in such structures may be chemically and/or physically bonded to each other. Examples of desirable mechanical properties in such nanofiber-based (or nanofiber-containing) formulations may include sufficient (for a given application) resistance to tension, puncture, compression, flexing and bending, resistance to pulse jets, shaking and vibrations. Examples of desirable thermal properties in such nanofiber-based (or nanofiber-containing) formulations may include high temperature (e.g., above around 250-350° C.) stability, where exposure to high temperatures for a prolonged time (e.g., in the range from around 10 sec to around 100 years, depending on the application) does not induce appreciable degradation in strength, toughness and elasticity. Examples of chemical properties in such nanofiber-based (or nanofiber-containing) formulations may include stability to chemical agents, such as gases, plasma and liquids (e.g., in the temperature range of about 25-200° C.) without appreciable changes in chemical composition, surface properties and mechanical properties. Examples of such gases may include but are not limited to gases used for oxidation and reduction (such as oxygen, ozone, hydrogen, hydrogen peroxide vapors, etc.) or other gasses suitable for surfaces activation, decontamination, and deactivation of various pathogens. Examples of such plasmas may include but are not limited to hydrogen peroxide, ozone, peracetic gas plasma or any other ionized plasma suitable for surface sterilization and deactivation of pathogens. Examples of such liquids include but are not limited to hydrogen peroxide solution, peracetic acid solution, hypochlorus acid or its salts solution, quaternary ammonium cation salts solutions or any other liquids suitable for surface sterilization and deactivation of pathogens. Examples of desirable physical properties in such nanofiber-based (or nanofiber-containing) formulations may include but not limited to high porosity, adjustable packing density, adjustable pore size, high dielectric constant (e.g., above around 5 at 1 MHz; in some designs above around 8 at 1 MHz) and tunable surface charge. In some designs, nanofiber-based (or nanofiber-containing) porous membranes may exhibit average pore size in the range from around 20 nm to around 2 micron (in some designs, from around 20 nm to around 200 nm). In some designs, nanofiber-based (or nanofiber-containing) porous membranes may greatly minimize (for example, by around 95.00000% to around 99.99990%, in some designs) permeation of small pathogens (e.g., viruses or bacteria) with average dimensions in the range from around 20 nm to around 600 nm. In such cases, it may be often beneficial to produce porous membranes with smaller average pore size (e.g., in the range from around 20 nm to around 400 nm; in some designs, from around 20 nm to around 100 nm). In some designs, such nanofiber-based (or nanofiber-containing) porous membranes may restrict the permeation of these small pathogens (e.g., viruses or small bacteria) by size exclusion or by adsorption on their surfaces or both. In some designs, such nanofiber-based (or nanofiber-containing) porous membranes that restrict the permeation of these small pathogens (e.g., viruses or small bacteria) may exhibit high air permeation (for example, have a "Gurley" number (air permittivity) in the range from around 5 seconds to around 2500 seconds for porous nanofiber-based membranes with the thickness in the range from around 5 micron to around 100 micron). In some designs, such nanofiber-based (or nanofiber-containing) porous membranes may be attached to another membrane (or fabric) with larger thickness and larger pore size. In some designs, such nanofiber-based (or nanofiber-containing) porous membranes may be sandwiched between layers or other membranes or fabric. In some designs, such nanofiber-based (or nanofiber-containing) porous membranes may be used to prevent access of viruses or bacteria to healing or open wounds while enabling supply of air. In some designs, such nanofiber-based (or nanofiber-containing) porous membranes may be used prevent access of viruses or bacteria to ear. In some designs, such nanofiber-based (or nanofiber-containing) porous membranes may be used reduce or prevent access of viruses or bacteria to mouth. In some designs, such nanofiber-based (or nanofiber-containing) porous membranes may be used to reduce or prevent access of viruses or bacteria to nasal cavity. In some designs, such nanofiber-based (or nanofiber-containing) porous membranes may be used to reduce or prevent access of viruses or bacteria to eyes. In some designs, such nanofiber-based (or nanofiber-containing) porous membranes may be used as a portion of masks (including, but not limited to so-called N95 or N96 or N97 or N98 or N99 or N100 masks). In some designs, such nanofiber-based (or nanofiber-containing) porous membranes may be used as a portion of air filtration systems in vehicles or buildings, particularly in places where people may be particularly sensitive (strongly affected by) various pathogens (bacteria or viruses), such as hospitals and other healthcare facilities, ambulance, as well as nursing homes and houses for elderly people.

Figure 5:
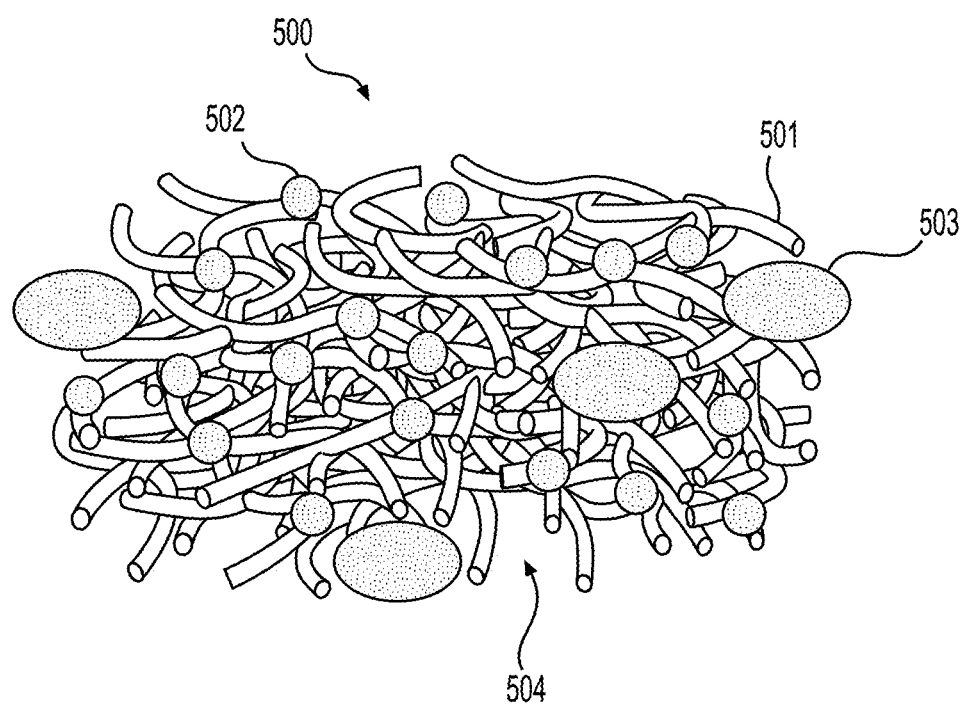
FIGS. 5-6 illustrate example structures of porous scaffolds or porous membranes that may be used according to various embodiments.

FIG. 5 illustrates a composition of a porous scaffold (or porous membrane) 500, where individual or bundled nanofibers 501 of suitable composition, dimensions and properties produce (e.g., flexible) porous material composition and where at least some of the neighboring nanofibers 501 may be bonded to each other by chemical or physical means or by using a binder 502, which may be selected from synthetic or naturally derived polymers (e.g., where natural polymers may including proteins, such as collagen tissue) and other suitable tissue-engineered biosynthetic matrices. In some designs, the tissue-engineered biosynthetic matrix materials may include synthetic or naturally derived amphiphilic polymers. In some designs, the tissue-engineered biosynthetic matrix materials may include synthetic or naturally derived hydrophilic polymers. In some designs, the tissue-engineered biosynthetic matrix materials may include synthetic or naturally derived hydrophobic polymers. A binder 502 may be coating the surface of nanofibers or may be in the form of the fibers or particles that bind the nanofibers together. In some designs, porous scaffolds (or porous membranes) 500 may include other suitable functional particles 503, which may, for example, comprise living cells, antibacterial or antiviral particles and other useful particles. In some designs, a significant portion (e.g., about 50-100 vol. %) of the pores 504 of the porous scaffold 500 may remain open and inter-penetrating.

Figure 6:
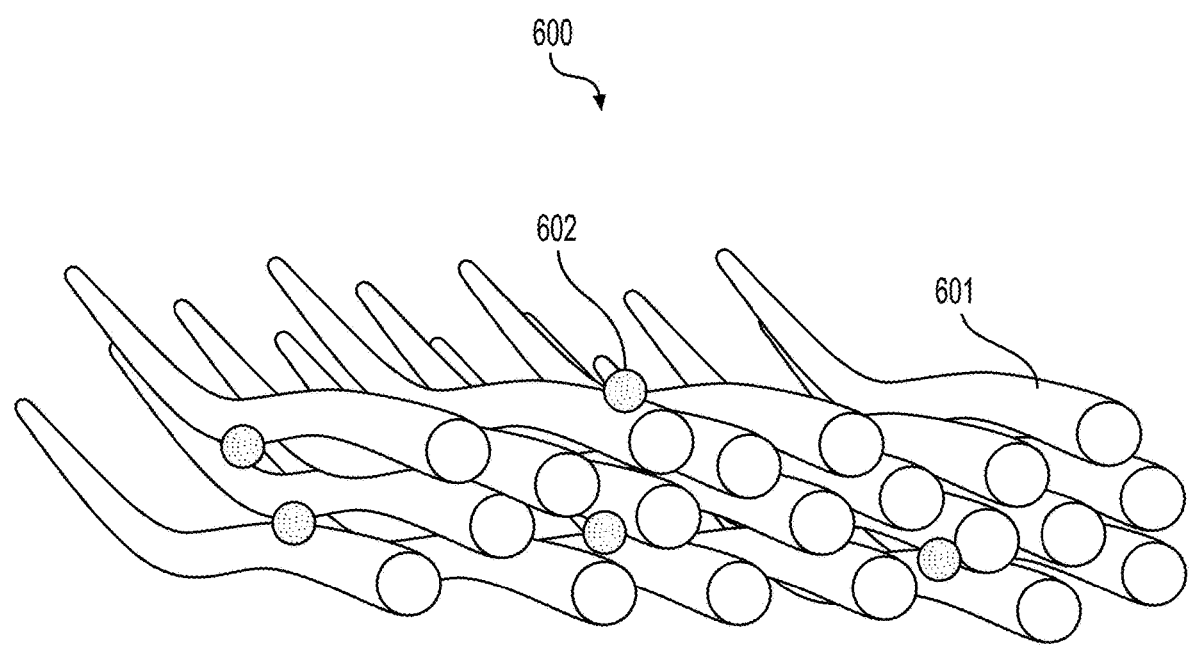

FIG. 6 illustrates a composition of a porous scaffold (or porous membrane) 600, where individual or bundled nanofibers 601 of suitable composition, dimensions and properties (which may be bonded with a suitable binder 602) are arranged with the same orientation in order, for example, to stimulate directional cell growth or in order to attain different mechanical properties along a preferred direction. Referring to FIGS. 5-6, the porous scaffolds or membranes 500-600 may comprise nanofibers with an average diameter in the range from around 1 nm to around 500 nm, an average length in the range from around 250 nm to around 500 μm, an average aspect ratio in the range from around 10 to around 100,000, an average total internal open pore volume in the range from around 0.01 cm$^3$/g to around 3 cm$^3$/g, and an average pore size in the range from around 0.5 nm to around 50 nm, where the nanofibers comprise an oxide or a salt of one, two, three or more metals selected from the group of Al, Ca, Mg, Li, Na, K, La, Y, Si, Fe and Zn, and where the porous scaffold or the porous membrane is configured for use in an environment where the nanofibers are exposed to a direct contact with extracellular body fluids. As noted above, the porous scaffold or the porous membrane may be configured to facilitate wound healing and minimize scar tissues, such as accelerating directional epithelial cell growth and by comprising one or more antiseptic agents (e.g., such as copper or copper oxide nanoparticles, silver or silver oxide nanoparticles, gold nanoparticles, zinc oxide nanoparticles, calcium oxide or hydroxide nanoparticles, magnesium oxide or hydroxide nanoparticles, iron oxide or hydroxide nanoparticles, yttrium oxide nanoparticles, titanium oxide nanoparticles, others and their various combinations) to combat bacteria or virus growth.

Figure 7:
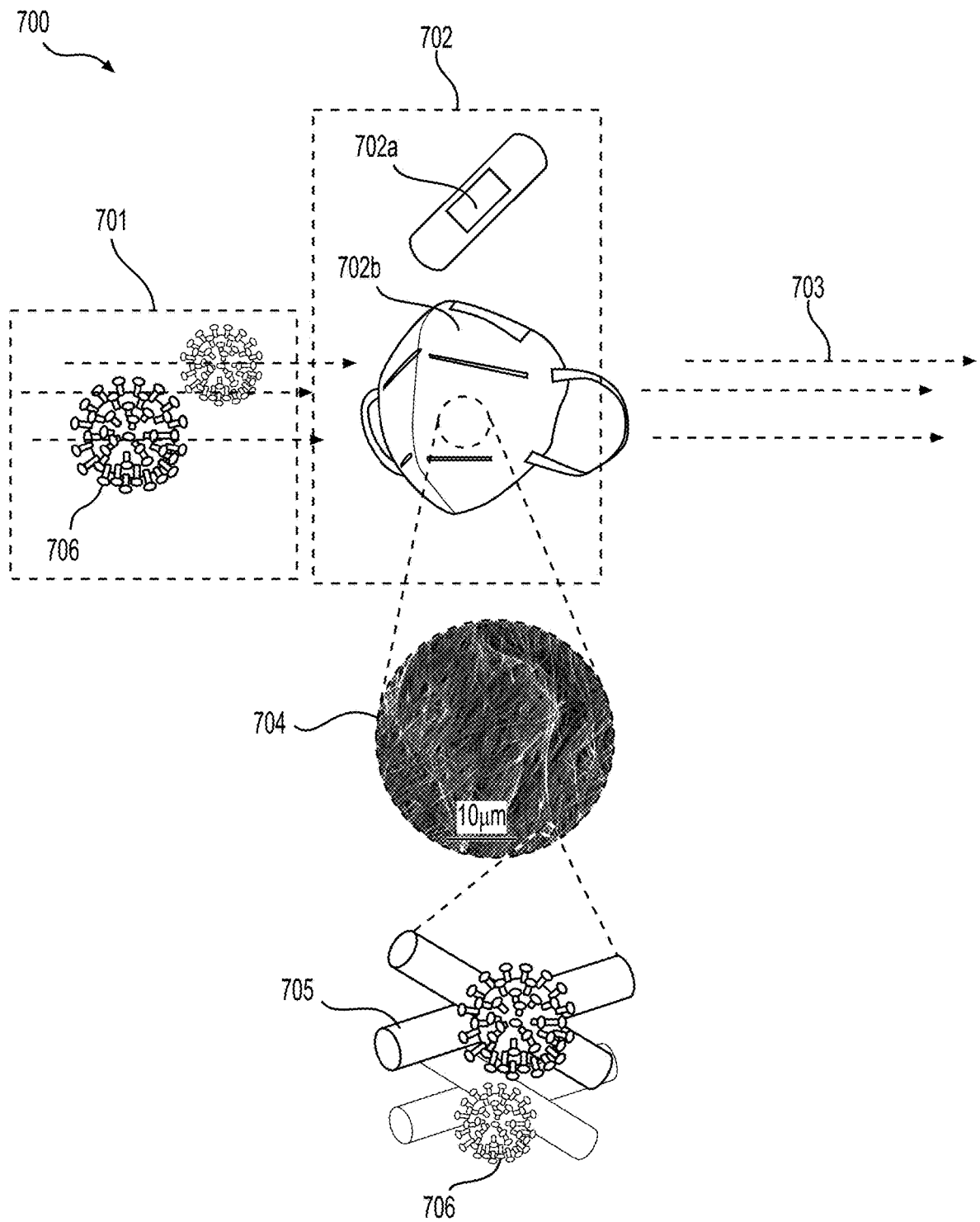
FIG. 7 illustrates example process of preventing the passage of pathogens (e.g., bacteria or viruses) through a device or material comprising nanofiber-based porous membrane.

FIG. 7 illustrates a filtration process 700 through a porous nanofiber-comprising membrane 704 that reduces or prevents permeation of pathogens (e.g., bacteria or virus) 706 while enabling the passage of air or oxygen or gas 703. In this schematic, particle pathogens—contaminated air 701 passes through a filtrating material or device 702 (e.g., a porous wound patch/bandage 702*a* or a porous mask 702*b*, etc.). Pathogen particles (e.g., bacteria or viruses) 706 become trapped at the nanofiber-membrane 704 by means of adsorption on the surface of nanofibers 705 (e.g., having high dielectric constant (e.g., above around 5 at 1 MHz) and high dipole moment on their surface) by means of size exclusion or electrostatic adsorption or chemical adsorption or other means or their various combination. In some designs, the porous nanofiber-comprising membrane 704 may be attached to a woven or nonwoven fabric or polymer filter or film in order to improve integrity or handling or to reduce cost of a filtrating material or device 702. In some designs, the nanofiber-comprising membrane may comprise suitable antiseptic agents (e.g., in the form of nanoparticles).

This description is provided to enable any person skilled in the art to make or use embodiments of the present invention. It will be appreciated, however, that the present disclosure is not limited to the particular formulations, process steps, and materials disclosed herein, as various modifications to these embodiments will be readily apparent to those skilled in the art. That is, the generic principles defined herein may be applied to other embodiments without departing from the spirit or scope of the disclosure.

The invention claimed is:

1. A nanofiber, comprising:
a compound comprising a primary metal, the primary metal comprising Al or Mg,
wherein the nanofiber is a non-agglomerated, individual nanofiber that exhibits a diameter in the range from around 1 nm to around 500 nm, a length in the range from around 250 nm to around 500 μm, an aspect ratio in the range from around 10 to around 100,000, a total pore volume in the range from around 0.01 cm$^3$/g to around 3 cm$^3$/g, and an average pore size in the range from around 0.5 nm to around 50 nm; and
an antigen and/or a vaccine adjuvant stored within one or more closed internal pores of the nanofiber.

2. The nanofiber of claim 1, wherein the nanofiber aspect ratio ranges from around 100 to around 10,000, the nanofiber length ranges from around 1.5 μm to around 150 μm, the nanofiber average pore size ranges from around 0.5 nm to around 20 nm, and the total pore volume is in the range from around 0.05 cm$^3$/g to around 1 cm$^3$/g.

3. The nanofiber of claim 1, wherein the nanofiber exhibits a positive surface charge in the range from around +2.00 mV to around +80.00 mV, as measured using Zeta-potential at a pH between about 7-8.

4. The nanofiber of claim 1,
wherein the nanofiber comprises a metal oxide and/or a metal salt.

5. The nanofiber of claim 4, wherein the metal oxide and/or the metal salt is selected from: (i) the metal oxide, (ii) a metal hydroxide, (iii) a metal oxyhydroxide, (iv) a metal sulfate, (v) a metal carbide, (vi) a metal phosphate, (vii) a metal hydroxy phosphate, (viii) a metal hydroxy phosphate sulfate, (ix) a metal phosphate sulfate, (x) a metal hydroxy sulfate, (xi) a metal carbonate, (xii) a metal carbonate phosphate, and (xiii) a metal silicate.

6. The nanofiber of claim 1, wherein Al constitutes between around 50 at. % to around 100 at. % of all the metals in the compound of the nanofiber.

7. The nanofiber of claim 1, wherein Mg constitutes between around 50 at. % to around 100 at. % of all the metals in the compound of the nanofiber.

8. The nanofiber of claim 1, wherein the compound comprises two or more metals with an atomic fraction of more than 0.01 at. % relative to all other metals in the compound.

9. The nanofiber of claim 1, wherein the nanofiber is derived from a metal-organic nanofiber.

10. The nanofiber of claim 9, wherein the metal-organic nanofiber is an alkoxide.

11. The nanofiber of claim 10, wherein the alkoxide is a methoxide, an ethoxide, an iso-propoxide, or n-propoxide.

12. The nanofiber of claim 11, wherein the metal-organic nanofiber is produced upon exposure of particles or chunks or bulk pieces of metals or Li-containing metal alloys to at least one alcohol.

13. The nanofiber of claim 1, further comprising:
additional antigen and/or additional vaccine adjuvant stored within one or more open internal pores of the nanofiber.

14. The nanofiber of claim 1, wherein the one or more closed internal pores of the nanofiber comprise the antigen.

15. The nanofiber of claim 1, wherein the one or more closed internal pores of the nanofiber comprise the vaccine adjuvant.

16. The nanofiber of claim 1, wherein the one or more closed internal pores of the nanofiber comprise the antigen and the vaccine adjuvant.

17. A nanofiber, comprising:
a compound comprising a primary metal, the primary metal comprising Al or Mg,
wherein the nanofiber is a non-agglomerated, individual nanofiber that exhibits a diameter in the range from around 1 nm to around 500 nm, a length in the range from around 250 nm to around 500 μm, an aspect ratio in the range from around 10 to around 100,000, a total pore volume in the range from around 0.01 cm³/g to around 3 cm³/g, and an average pore size in the range from around 0.5 nm to around 50 nm; and an antigen and/or a vaccine adjuvant stored within one or more closed internal pores of the nanofiber, wherein the compound further comprises:

a secondary metal selected from Ca, Li, Na, K, La, Y, Si, Fe and Zn.

18. The nanofiber of claim 17, wherein Ca constitutes between around 50 at. % to around 100 at. % of all the metals in the compound of the nanofiber.

19. The nanofiber of claim 17, wherein Zn constitutes between around 50 at. % to around 100 at. % of all the metals in the compound of the nanofiber.

20. A porous scaffold or a porous membrane, comprising:
nanofibers, each of the nanofibers being an instance of the nanofiber of claim 1, wherein the porous scaffold or the porous membrane is configured for use in an environment where the nanofibers are exposed to a direct contact with extracellular body fluids.

21. The porous scaffold or porous membrane of claim 20, wherein the porous scaffold or the porous membrane is configured to facilitate wound healing.

22. The porous scaffold or porous membrane of claim 21, wherein the nanofibers comprise one or more antiseptic agents to combat bacteria or virus growth.

* * * * *